(12) United States Patent  
Gomez et al.

(10) Patent No.: US 11,266,475 B2  
(45) Date of Patent: Mar. 8, 2022

(54) REPOSITIONING SYSTEM FOR A REMOTELY CONTROLLABLE MANIPULATOR AND RELATED METHODS

(71) Applicant: Intuitive Surgical Operations, Inc., Sunnyvale, CA (US)

(72) Inventors: Daniel H. Gomez, Los Gatos, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 368 days.

(21) Appl. No.: 16/484,299

(22) PCT Filed: Dec. 11, 2017

(86) PCT No.: PCT/US2017/065522
§ 371 (c)(1),
(2) Date: Aug. 7, 2019

(87) PCT Pub. No.: WO2018/147930
PCT Pub. Date: Aug. 16, 2018

(65) Prior Publication Data
US 2021/0128262 A1    May 6, 2021

Related U.S. Application Data

(60) Provisional application No. 62/456,430, filed on Feb. 8, 2017.

(51) Int. Cl.
*A61B 34/00* (2016.01)
*A61B 34/30* (2016.01)
(Continued)

(52) U.S. Cl.
CPC .............. *A61B 34/74* (2016.02); *A61B 34/35* (2016.02); *A61B 2034/302* (2016.02); *A61B 2090/508* (2016.02); *A61B 2090/571* (2016.02)

(58) Field of Classification Search
CPC combination set(s) only.
See application file for complete search history.

(56) References Cited

U.S. PATENT DOCUMENTS 5,279,309 A    1/1994   Taylor et al.
5,695,500 A   12/1997   Taylor et al.
(Continued)

FOREIGN PATENT DOCUMENTS

WO    WO-2018052795 A1    3/2018
WO    WO-2018067696 A1    4/2018

OTHER PUBLICATIONS

Extended European Search Report for Application No. EP17896089.4 dated Jan. 17, 2020, 9 pages (P00806-EP).
(Continued)

*Primary Examiner* — Scott Luan
(74) *Attorney, Agent, or Firm* — Fish & Richardson P.C.

(57) ABSTRACT

A computer-assisted system comprises a manipulator configured to support a tool, a lockable joint, and a controller. The manipulator extends distally from a base and comprises a distal portion. The lockable joint is coupled to the base and located proximally relative to the base. The controller is operably coupled to a powered joint. The powered joint is located distally relative to the base. The controller is configured to perform operations. The operations comprise: driving the powered joint to move the distal portion while the lockable joint is locked, and driving the powered joint to move the base while the lockable joint is unlocked and a position of the distal portion is externally maintained. A method includes processes for operating a computer-assisted system. A method includes determining a desired motion envelope for a tool supported by a manipulator, and positioning a base of the manipulator based on the desired motion envelope.

27 Claims, 10 Drawing Sheets

(51) Int. Cl.
  *A61B 34/35* (2016.01)
  *A61B 90/50* (2016.01)
  *A61B 90/57* (2016.01)

(56) References Cited

U.S. PATENT DOCUMENTS

| | | |
|---|---|---|
| 2007/0013336 A1 | 1/2007 | Nowlin et al. |
| 2011/0277775 A1 | 11/2011 | Holop et al. |
| 2014/0039517 A1 | 2/2014 | Bowling et al. |
| 2016/0081753 A1 | 3/2016 | Kostrzewski et al. |
| 2016/0113728 A1 | 4/2016 | Piron et al. |

OTHER PUBLICATIONS

International Search Report and Written Opinion for Application No. PCT/US2017/065522, dated Jul. 5, 2018, 23 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

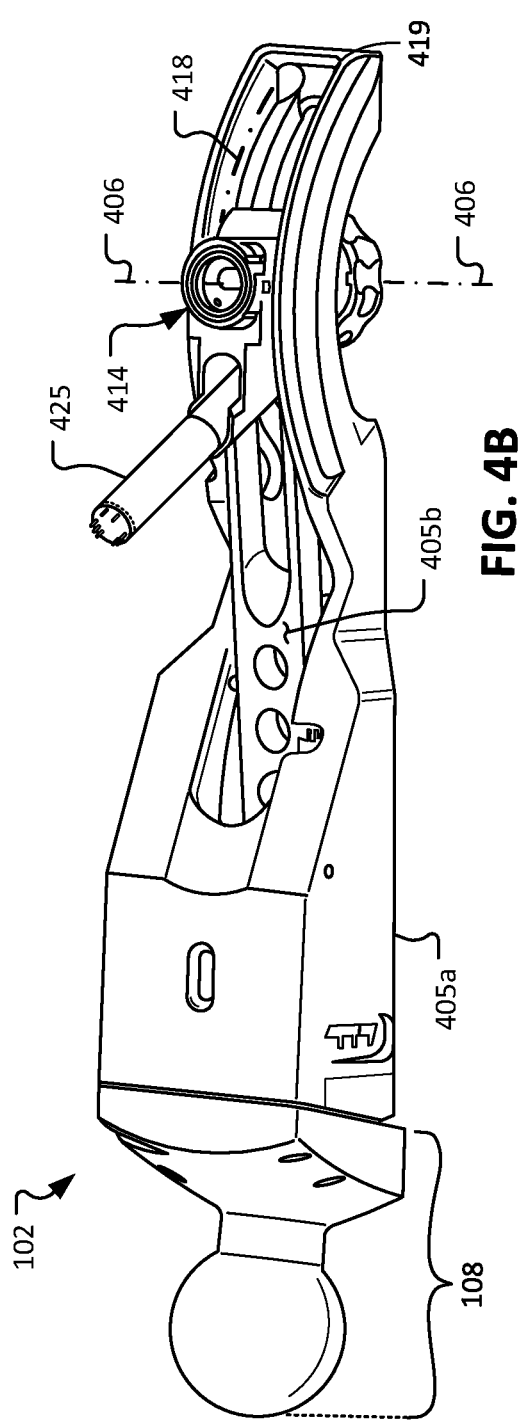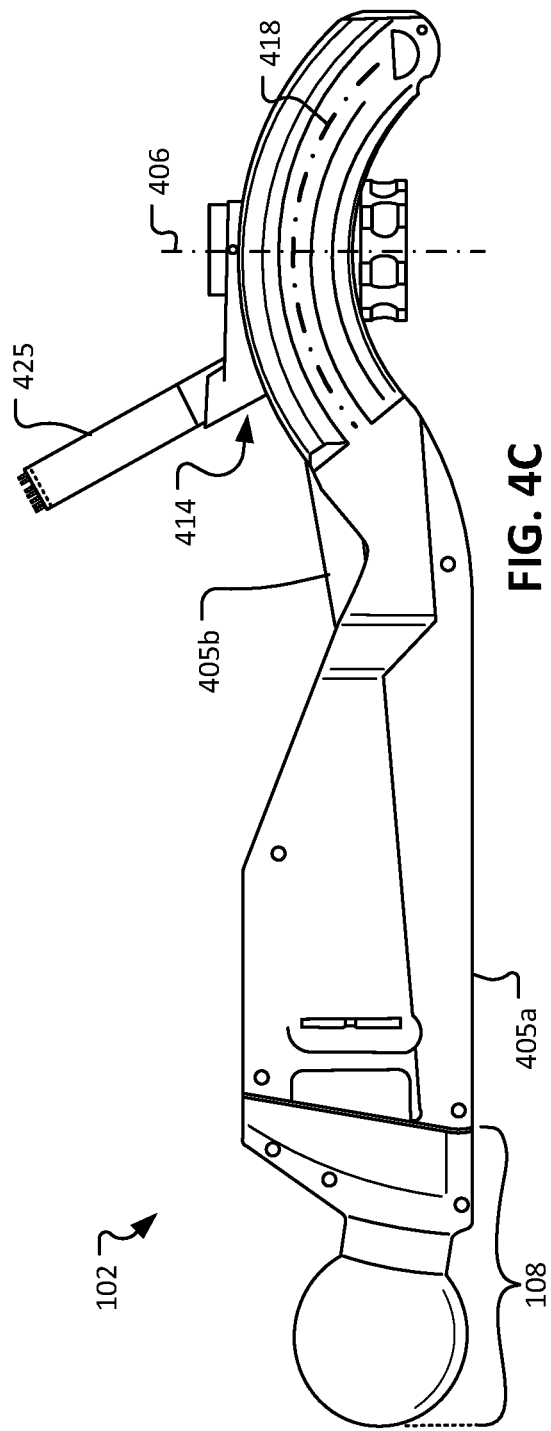

REPOSITIONING SYSTEM FOR A REMOTELY CONTROLLABLE MANIPULATOR AND RELATED METHODS

CROSS-REFERENCES TO RELATED APPLICATIONS

This application is a U.S. National Stage Application under 35 U.S.C § 371 and claims the benefit of International Patent Application No. PCT/US2017/065522, filed on Dec. 11, 2017, which claims the benefit of U.S. Provisional Application No. 62/456,430, filed on Feb. 8, 2017. The disclosures of the prior applications are considered part of and are incorporated herein by reference in the disclosure of this application.

TECHNICAL FIELD

This specification relates to a system for a manipulator such as a remotely controllable manipulator.

BACKGROUND

Robotic systems can include robotic manipulators to manipulate tools for performing a task at a work site. The robotic manipulator can include two or more links coupled together by one or more joints. The joints can be active joints that are actively controlled. The joints can also be passive joints that may comply with movement of the active joints as the active joints are actively controlled. Such active and passive joints may be revolute or prismatic joints. The configuration of the robotic manipulator may then be determined by the positions of the joints, the structure of the robotic manipulator, and the coupling of the links.

Robotic systems include industrial and recreational robotic systems. Robotic systems also include medical robotic systems used in procedures for diagnosis, non-surgical treatment, surgical treatment, etc. As a specific example, robotic systems include minimally invasive, computer-assisted, robotic surgical systems in which a surgeon can operate on a patient from bedside or a remote location. Telesurgery refers generally to surgery performed using surgical systems where the surgeon uses some form of remote control, e.g., a servomechanism, to manipulate surgical tool movements rather than directly holding and moving the surgical tools by hand. A robotic surgical system usable for telesurgery can include a remotely controllable robotic manipulator. Operators can remotely control motion of the robotic manipulator. Operators can also manually move pieces of the robotic surgical system into positions within a surgical environment. For example, a surgeon, a surgical assistant, or other operator can push or pull the equipment by hand such that the equipment moves along a floor surface of the surgical environment.

SUMMARY

In one aspect, a computer-assisted system comprises a manipulator configured to support a tool, a lockable joint, and a controller. The manipulator extends distally from a base and comprises a distal portion. The lockable joint is coupled to the base and located proximally relative to the base. The controller is operably coupled to a powered joint. The powered joint is located distally relative to the base. The controller is configured to perform operations. The operations comprise: driving the powered joint to move the distal portion while the lockable joint is locked, and driving the powered joint to move the base while the lockable joint is unlocked and a position, an orientation, or both position and orientation parameters is externally maintained.

In another aspect, a method for operating a computer-assisted system comprises driving a powered joint to move a base while a lockable joint is unlocked and a position, an orientation, or both position and orientation parameters of a distal portion of a manipulator is externally maintained, and driving the powered joint to move the distal portion while the lockable joint is locked. The computer-assisted system comprises the manipulator and the lockable joint. The manipulator extends distally from a base. The lockable joint is coupled to the base and located proximally relative to the base. The powered joint is located distally relative to the base.

In another aspect, a non-transitory machine-readable medium comprises a plurality of machine-readable instructions. These instructions are adapted, when executed by one or more processors are, to cause the one or more processors to perform any of the methods disclosed herein.

For example, in one aspect, these instructions are adapted to cause one or more processors to perform a method for operating a computer-assisted system. The computer-assisted system comprises a manipulator and a lockable joint. The manipulator extends distally from a base. The lockable joint is coupled to the base and located proximally relative to the base. The method comprises: determining a desired location for the base, driving a powered joint to backdrive the base toward the desired location while the lockable joint is unlocked and a position, an orientation, or both position and orientation parameters of a distal portion of the manipulator is externally maintained, and (after the lockable joint is locked) driving the powered joint to move the distal portion. The powered joint is located distally relative to the base.

In yet another aspect, a computer-assisted surgical system includes a remotely controllable manipulator. The manipulator extends from a base of the manipulator to a distal portion including a coupling configured to support a surgical tool. The surgical system further includes a lockable joint at the base of the manipulator. A powered joint distal to the base is drivable to move the surgical tool relative to a reference point within a motion envelope while the lockable joint is locked. The motion envelope is defined in part by a position of the base relative to the reference point. The surgical system further includes a controller operably connected to the powered joint. The controller is configured to change the motion envelope of the surgical tool by driving the powered joint, while the lockable joint is unlocked and while a position of the surgical tool relative to the reference point is maintained, to adjust the position of the base relative to the reference point.

In another aspect, a method includes determining a desired motion envelope for a surgical tool supported by a remotely controllable manipulator. The method further includes driving a powered joint distal to a base of the manipulator to reposition the base relative to an operating table such that a motion envelope of the surgical tool is adjusted based on the desired motion envelope while the base is unlocked and while a position of the surgical tool is maintained.

Some implementations may include one or more of the features described below and herein elsewhere, including any appropriate combination of the implementations described below.

In various implementations, the pose of the distal portion is externally maintained by maintaining, for a part of the distal portion: a position, an orientation, one or more position parameters, one or more orientation parameters, both position and orientation, or a combination of position and orientation parameters.

In some implementations, the position of the distal portion is externally maintained relative to a reference point, driving the powered joint to move the distal portion moves the distal portion relative to the reference point, and driving the powered joint to move the base moves the base relative to the reference point. In some implementations, the reference point corresponds to a location of an access port through which the tool accesses a work site. In some implementations, the access port is a minimally invasive access port or an entry to a natural orifice of a patient.

In some implementations, a position of the base is maintained by the lockable joint. For example, locking the lockable joint, or locking a plurality of lockable joints including the lockable joint, locks the position of the base. In some implementations, the position of the distal portion is externally maintained by maintaining a position of the tool or a position of a cannula coupled to the manipulator.

In some implementations, driving the powered joint while the lockable joint is unlocked and the position of the distal portion is externally maintained moves the base by back-driving with the powered joint.

In some implementations, the driving of the powered joint to move the base is slowed or stopped in response a determination that the position of the distal portion is not externally maintained.

In some implementations, the computer-assisted system further comprises an actuation module. The manipulator is configured to couple to the actuation module and support the tool through the actuation module. In some implementations, and the actuation module is configured to translate the tool along a longitudinal axis of the tool, and to drive an end effector of the tool. In some implementations, the actuation module comprises the powered joint.

In some implementations, the manipulator comprises the powered joint.

In some implementations, the method further comprises, or the operations further comprise, driving the powered joint to center the tool within a range of motion of the tool. In some implementations, the driving of the powered joint to center the tool is based on a user selection. In some implementations, driving the powered joint to center the tool comprises driving the powered joint to adjust the position of the base based on a pointing direction of the tool.

In some implementations, driving the powered joint to move the base comprises determining a desired motion envelope, and driving the powered joint to move the base toward a position that provides the desired motion envelope. In some implementations, driving the powered joint to move the base comprises determining a desired location for the base, and driving the powered joint to move the base toward the desired location. The system may stop moving the base once the base reaches, or is within some tolerance of, the position that provides the desired motion envelope or the desired location for the base; or, the system may stop moving the base in response to some other criteria, such as in response to forces or deflections indicative of collision, to a determination of an inability to reach the base position that provides the desired motion envelope or the desired base location, to user input, to lack of user presence, etc.

In various implementations, the desired motion envelope or the desired location for the base is determine based on one or more of the following: a likelihood of collision of the manipulator, a pose of the manipulator relative to a pose of a second manipulator of the computer-assisted system, a motion envelope of a setup joint of the manipulator, a type of operation to be performed, a likelihood of collision of the manipulator. The second manipulator may be coupled to the same base as the first manipulator, or to a second base separate and moveable relative to the base of the first manipulator.

In some implementations, driving the powered joint to move the base while the lockable joint is unlocked comprises driving the powered joint to adjust the position of the base based on a pointing direction of the tool. In some implementations, driving the powered joint based on a pointing direction of the tool comprises driving the powered joint while an insertion axis of the tool is directed toward a target. In some implementations, adjusting the position of the base based on the pointing direction of the tool facilitates centering the tool within its range of motion or motion envelope.

In some implementations, the operations further comprise, or the method further comprises driving a second powered joint coupled to the base and located distally relative to the base. For example, the powered joint and a second powered joint are both driven to move the distal portion while the lockable joint is locked. And, the powered joint and a second powered joint are both driven to move the base while the lockable joint is unlocked and the position of the distal portion is externally maintained.

In some implementations, the computer-assisted system further comprises one or more additional lockable joints that are unlocked when driving the powered joint to move the base, and/or are locked when driving the powered joint to move the base. For example, in one implementation, the computer-assisted system further comprises a second lockable joint, and driving the powered joint to move the base comprises driving the powered joint to reposition the lockable joint and the second lockable joint while both the lockable joint and the second lockable joint are unlocked.

In some implementations, the computer-assisted system further a setup assembly configured to couple the base to a table, where the setup assembly comprises the lockable joint.

In some implementations, the computer-assisted system further comprises a sensor configured to generate a signal in response to detecting that the position of the distal portion is externally maintained. And, the powered joint is driven to move the base in response to the signal.

In some implementations, the computer-assisted system further comprises a sensor configured to generate a signal in response to detecting that the lockable joint is locked. And, the powered joint is driven to move the distal portion in response to the signal.

In some implementations, the lockable joint is manually locked, manually unlocked, or both manually locked and unlocked.

In some implementations, the method further comprises, or the operations further comprise, unlocking the lockable joint after driving the powered joint to move the base. In some implementations, the method comprises, or the operations comprise, selectively unlocking or locking the lockable joint while driving the powered joint to move the base, while the position of the distal portion is externally maintained.

In some implementations, the method further comprises, or the operations further comprise, inhibiting motion of the base in response to a determination that a motion envelope of the tool is approaching a desired motion envelope for the tool.

In some implementations, the controller is configured to change the motion envelope of the surgical tool by driving the powered joint to backdrive the base.

In some implementations, driving the powered joint includes backdriving the base.

In some implementations, the coupling is configured to receive an actuation module operable to drive an end effector of the surgical tool. In some cases, the surgical system further includes the actuation module. The actuation module is, for example, mounted to the coupling of the manipulator, and the actuation module is configured to translate the surgical tool along a longitudinal axis of the surgical tool and to drive the end effector of the surgical tool when the surgical tool is mounted to the actuation module. In some cases, the powered joint includes a powered joint between the actuation module and the surgical tool.

In some implementations, the remotely controllable manipulator includes the powered joint.

In some implementations, a position of the base is fixed relative to the reference point when the lockable joint is locked, and the position of the base is movable relative to the reference point to change the motion envelope of the surgical tool when the lockable joint is unlocked.

In some implementations, the controller is configured to drive the powered joint to center the surgical tool within a range of motion of the surgical tool. In some cases, the controller is configured to drive the powered joint to center the surgical tool based on a user selection.

In some implementations, the controller is configured to change the motion envelope of the surgical tool in accordance to a desired motion envelope based on a type of surgical operation to be performed by the surgical system.

In some implementations, controller is configured to change the motion envelope of the surgical tool in accordance to a desired motion envelope based on a likelihood of collision of the manipulator with an obstacle.

In some implementations, the controller is configured to the drive the powered joint to adjust the position of the base while an insertion axis of the surgical tool is directed toward a target anatomy of a patient, the patient being fixed relative to the reference point.

In some implementations, the manipulator includes a linkage extending between the base and the surgical tool, and the controller is configured to change the motion envelope of the surgical tool by moving the linkage relative to the base.

In some implementations, the controller is configured to drive first and second powered joints to adjust the motion envelope of the surgical tool.

In some implementations, the surgical system further includes a setup assembly including the lockable joint. The setup assembly, for example, supports the manipulator relative to the reference point. The controller is, for example, configured drive the powered joint to reposition the setup joint while the base is movable relative to the reference point, while the setup joint is movable relative to the reference point, and while the position of the surgical tool is maintained.

In some implementations, the controller is configured to drive the powered joint to perform a surgical operation after changing the motion envelope of the surgical tool and after the lockable joint is locked.

In some implementations, the controller is configured to drive the powered joint to adjust the position of the base while a user directs the surgical tool toward target anatomy of a patient.

In some implementations, determining the desired motion envelope includes determining the desired motion envelope based on a motion envelope of a setup joint of the manipulator.

In some implementations, determining the desired motion envelope includes determining the desired motion envelope based on a type of surgical operation to be performed. In some cases, repositioning the base of the manipulator includes driving a powered joint of the manipulator. The method further includes, for example, driving the powered joint to perform the surgical operation on a patient.

In some implementations, determining the desired motion envelope includes determining the desired motion envelope based on a likelihood of collision of the manipulator with an obstacle.

In some implementations, repositioning the base of the manipulator includes repositioning the base of the manipulator while a setup joint of the manipulator is unlocked.

Advantages of the foregoing may include, but are not limited to, those described below and herein elsewhere. The base can be repositioned such that the surgical tool can more easily reach target anatomy during a surgical procedure. For a manipulator system including a setup assembly and the manipulator, the base of the manipulator can be repositioned without a human operator having to manually reposition the base or the setup assembly of the manipulator system. During repositioning of the base, the motion envelope of the surgical tool can be adjusted to reduce a likelihood that the manipulator contacts objects within the surgical environment.

In some examples, actuators in addition to the actuators to reposition the surgical tool are not necessary to reposition the base. The actuators that are used to reposition the surgical tool are also used to reposition the base. These actuators can be actuators kinematically positioned between the surgical tool and the base of the manipulator, thereby preventing a need for external actuators to drive the base.

Although the specific examples presented in this disclosure often discuss surgical examples, the techniques disclosed are also applicable to non-surgical use. For example, they may be used with and improve general or industrial robotic operations, such as those use in manipulating work pieces. These techniques may also be used with and improve medical robotic operations for diagnoses and non-surgical treatment.

Further, although the specific examples presented in this disclosure often discuss teleoperational robotic systems and remotely controllable arms, the techniques disclosed are also applicable to robotic systems that are directly and manually moved by operators, in part or in whole. For example, these techniques can be applied to robotic systems designed to help steady a tool held by the robotic arm while the tool is manipulated hand of an operator.

As another example, any of the controllable arms discussed herein may be configured to allow direct manipulation, and accept operator instruction through input directly applied to a link or a joint of the manipulator.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

FIG. 4B is a top perspective view of the manipulator of FIG. 4A.

FIG. 4C is a side view of the manipulator of FIG. 4A.

Like reference numbers and designations in the various drawings indicate like elements.

DETAILED DESCRIPTION

Figure 1:
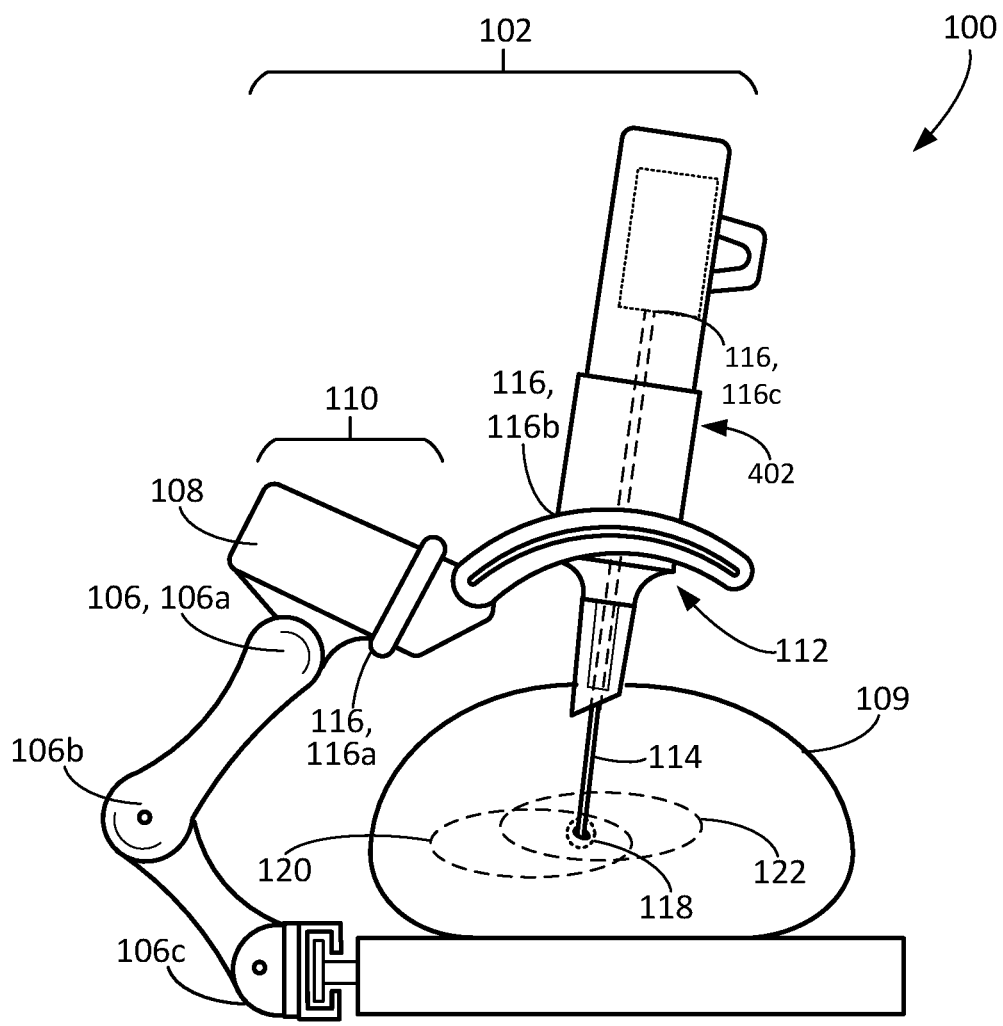
FIG. 1 is a side view of an example computer-assisted system with a manipulator.

Although some of the examples described herein refer to surgical procedures or tools, or medical procedures and medical tools, the techniques disclosed apply to non-medical procedures and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical, medical treatment or diagnosis procedures.

Further, although some of the examples presented in this disclosure discuss teleoperational robotic systems or remotely operable systems, the techniques disclosed are also applicable to computer-assisted systems that are directly and manually moved by operators, in part or in whole. For example, these techniques can be applied to robotic systems designed to help steady a tool held by the robotic arm while the tool is manipulated by a hand of an operator. As another example, the manipulators discussed herein may be configured to allow direct manipulation, and accept operator instruction through input directly applied to a link or a joint of the manipulator.

"And/or" is used herein to indicate either or both of two stated possibilities. For example, "a position and/or orientation" is used to indicate a position, an orientation, or a combination of both position and orientation parameters.

"Pose" is used herein to indicate one or more position parameters, one or more orientation parameters, or any combination of position and orientation parameters. For example, a "pose" of the distal portion of a manipulator (or of an item held by the manipulator) can comprise one or more position parameters, one or more orientation parameters, or any combination of position and orientation parameters, of the distal portion (or of the item). Thus, although the specific examples presented in this disclosure often discuss for simplicity maintaining the position of a distal portion of a manipulator, the techniques described herein are usable in other respects as well. For example, these techniques may be used to maintain a position along one or more axes or in 3-D space, an orientation about one or more axes or in 3-D space, or a combination of position and orientation parameters for a distal portion of a manipulator, or for an item supported by the manipulator (such as a cannula or tool or other device). As a specific example, these techniques may be used to maintain a position in 3D space and a rotation in 3D space, such that no translation or rotation occurs in that 3D space.

"Reposition" is used herein to indicate changing the position, the orientation, or both the position and orientation. For example, "repositioning" of the base comprises translating or rotating the base in some way, and thus changing one or more position or orientation parameters of the base.

"Linkage" is used herein to indicate a structure comprising a single link, at least one link, or multiple links as applicable given the context.

"Tool" is used herein to encompasses both general or industrial robotic tools and specialized robotic medical instruments (including robotic surgical instruments and robotic medical instruments for diagnoses and non-surgical treatment). Examples tools (e.g. of tool 114 described in conjunction with FIG. 1) include: cameras or other imaging tools utilizing fluoroscopic, radiation, ultrasonic, sonic, optical, or other techniques; suction, irrigation, grasping, cutting, measuring, and other tools of various sizes, shapes and functions; and tools that apply energies such as RF, microwave, ultrasound, etc.

FIG. 1 depicts a side view of a computer-assisted system in an environment 10. In this particular example, the computer-assisted system comprises a manipulator relocation system 100. The environment 10 may be an industrial, recreational, training, or surgical or other medical environment. The relocation system 100 includes a manipulator 102 and a controller 104. The manipulator 102 may also be referred to as the manipulator 102. In various implementations, the manipulator 102 is directly operated, or teleoperated in whole or in part. In various implementations, the manipulator 102 is controlled remotely. In the example shown in FIG. 1, the manipulator 102 extends from a base 108, at a proximal portion 110, to a distal portion 112 that can support a tool 114. The tool 114 may be a removable tool. In some implementations, a coupling of the manipulator provides an interface that allows the removal of the tool from the manipulator (e.g. manipulator 102 described in conjunction with FIG. 1). For example, in some implementations, the coupling provides a tool/manipulator interface that allows rapid removal of the tool and mounting of the same tool or a different tool.

The lockable joint 106 is located proximal to a base 108 of the manipulator 102, and is a lockable and unlockable joint. In various implementations, the lockable joint 106 is configured to be manually locked, manually unlocked, automatically locked, automatically unlocked, or a combination of the foregoing. In some implementations, the lockable joint 106 is locked at a default, and intentional or continuous input by a user is required for unlocking the lockable joint 106. In the FIG. 1 example, the lockable joint 106 is located at the base 108, and at the proximal portion 110 of the manipulator 102.

Where the joint 106 is the only joint between the base 108 and a structure, locking the joint 106 locks a pose of the base 108 relative to that structure. That is, the locked pose of the base 108 is kept within narrow tolerances as limited by the design and operation of the joint 106 and the structure. Thus, the pose of the base may be referenced to a frame of reference, and held stationary relative to that frame of reference. Example frames of reference include coordinate frames fixed relative to the environment 10, specific features of the workpiece or work site, access ports to the work site, a part of the manipulator 102 prior to repositioning, etc. If the environment 10 is a surgical or other medical environment, examples of where frames of reference may be attached include patient tissue, patient anatomical features, a surface supporting the patient, a floor surface, the surgical environment, etc.

In some implementations, the locking the joint 106 holds the base fixed relative to a reference point 118. Where the reference point 118 is fixed relative to the environment 10, locking the joint 106 holds the base fixed relative to the environment 10. In some medical implementations, The reference point 118 corresponds to a point fixed relative to a workpiece 109. The reference point 118 can, for example, correspond to a point on an insertion site or a port on the workpiece 109 through which the tool 114 is, or will be, inserted, a point fixed relative to a floor surface in the environment 10, a point fixed relative to an operating table in the environment 10, etc. In a surgical or other medical context, the workpiece 109 may comprise a part of a patient, and an insertion site or port may comprise an incision or natural orifice of the patient.

A powered joint 116 distal to the base 108 can be driven by an actuator operable by the controller 104 to cause relative repositioning of the base 108, of a portion of the manipulator 102 such as the distal portion 112 of the manipulator 102, and/or of an item coupled to the manipulator such as a cannula or the tool 114 when mounted. The powered joint 116 is positioned in kinematic series with one or more linkages of the manipulator 102, for example, between where the tool 114 would be when supported by the manipulator 102 and the base 108. For example, the powered joint 116 can join two of the linkages of the manipulator 102, or join a linkage and a device mounted to the distal portion 112 of the manipulator 102. The powered joint 116 is, in an implementation, for example, positioned between the proximal portion 110 and the distal portion 112 of the manipulator 102. When the tool 114 is supported on the distal portion 112 of the manipulator 102, the tool 114 and the base 108 move relative to one another when the powered joint 116 is driven. The controller 104, for example, operates the actuator coupled to the powered joint 116 to drive the powered joint 116 and cause relative movement between the base 108 and the distal portion 112, and hence the tool 114 if mounted to the distal portion of the manipulator 102. During processes and operations described herein, the controller 104 operates the powered joint 116 to move the base 108 relative to the distal portion 112 (or an item coupled to the manipulator, such as a cannula or the tool 114 when mounted). To adjust the position (and/or orientation) of the base 108, the controller 104 drives the powered joint 116 while both: (a) the joint 106 coupled to the base 108 is unlocked, and (b) a position (and/or orientation) of the distal portion 112 (or an item coupled to the manipulator) is externally maintained.

To reposition the base 108, the controller 104 can drive the powered joint 116 by selectively activating one or more actuators that move the powered joint 116. The driven motion of the powered joint 116 can backdrive joint 106, and thus move the base 108. In some cases, this backdriving of the base 108 is achieved with only the driven motion of the powered joint 116, and no motion of any other powered joint(s) of the manipulator 102. In some cases, this backdriving of the base 108 is achieved with the driven motion of the powered joint 116 complemented by additional driven motion of one or more other powered joint(s) of the manipulator 102. In some cases, this backdriving of the base 108 is achieved with the backdriven motion of only the lockable joint 106. In some cases, this backdriving of the base 108 is achieved with the backdriven motion of the lockable joint 106 and other backdriven motion of one or more other lockable joint(s) of the manipulator 102.

Thus, the relocation system 100 is an example computer-assisted system that comprises one or more manipulators (e.g. manipulator 102), each manipulator configured to support a tool (e.g. tool 114). The computer-assisted system comprises one or more lockable joints (e.g. joint 116) and a controller. (e.g. controller 104). Each of the manipulators extends distally from a base (e.g. base 108) and comprises a distal portion (e.g. distal portion 112). The one or more lockable joints are coupled to the base and located proximally relative to the base. The controller 104 is operably coupled to one or more powered joints (e.g. powered joint 106). The powered joint is located distally relative to the base. The controller 104 is configured to perform a method or a set of operations, comprising the following: driving at least one powered joint to move the distal portion while at least one lockable joint is locked, and driving at least one powered joint to move the base while at least one lockable joint is unlocked and a position of one or more distal portions are externally maintained.

In some implementations, the controller 104 drives the powered joint 106 to move the base 108 is toward a desired location (and/or orientation) for base. The desired location (and/or orientation) may be determined based on a desired motion envelope 122 or any other appropriate criteria. In some implementations, the controller 104 drives the powered joint 106 to move the base 108 toward a position (and/or an orientation) that provides a desired motion envelope 122 for the tool 114. In some implementations, the controller 104 stops moving the base 108 once the base 108 reaches, or is within some tolerance of, the position (and/or orientation) that provides the desired motion envelope or the desired location for the base 108. In some implementations, the controller 104 may stop driving the powered joint 116, or stop moving the base 108, before achieving the desired base location or the desired motion envelop 122. Such stopping may be in response to some other criteria, such as in response to forces or deflections indicative of collision, to a determination of an inability to reach the position (and/or orientation) that provides the desired motion envelope or the desired location for the base 108, to user input, to lack of user presence, and the like.

In some implementations, after the base has been moved by backdriving with the powered joint 116, the lockable joint 106 is unlocked to allow driving of the powered joint 116 to move the distal portion 112 (or device held by the distal portion 112, such as a cannula or the tool 114). In various implementations, the lockable joint 106 is unlocked manually or in response to a user input indicating that the lockable joint should be unlocked. In some implementations, the controller 104 automatically causes the lockable joint to be unlocked automatically after achieving a desired base location or a desired motion envelope 122. During the repositioning of the base 108, a distal portion 112 of the manipulator 102 (or an item supported by the manipulator 102, such as a cannula or a tool 114 if mounted to the manipulator 102) can be externally maintained in a desired position (and/or orientation) within the environment 10. The position (and/or orientation) may be maintained relative to any appropriate reference. In some implementations, the reference comprises a reference point (e.g. reference point 118), one or more reference directions, or a reference frame. In some implementations, a reference consisting of a single point without orientation information can be sufficient in implementations where only position is maintained. In some implementations, the reference comprises one or more reference directions but not a reference location; for example, the one or more reference directions may be based on the three-dimensional orientation of the distal portion 112 immediately prior to a beginning of the repositioning process. A set of direction(s) without a reference location can be sufficient in implementations where only the orientation(s) corresponding to the set of direction(s) are maintained. In some implementations, the reference comprises both a reference location and one or more reference directions; such a reference may be used when position and one or more orientation parameters are maintained. In some implementations, the reference comprises a full reference frame sufficient to define location and orientation in three-dimensional space.

The position is maintained when the position is kept within an acceptable range of position changes. For example, in some implementations, the acceptable range of position changes is zero, and maintained the position involves keeping the position completely unchanged. In some implementations, the acceptable range of position changes is nonzero, and is based on the limits of the system's design; the position is maintained as close to unchanging as possible given mechanical, electrical, and computational tolerances and errors. In some implementations, the acceptable range of position changes is nonzero, and includes bounds based on operating conditions. For example, in some cases, the acceptable range of position changes is on the order of millimeters or centimeters, and is set to avoid damage to a work piece or human tissue. In some cases, the acceptable range of position changes is larger. In some cases, the acceptable range of position changes differ among different translational degrees of freedom.

Similarly, the orientation is maintained when the orientation is kept within an acceptable range of orientation changes. In various implementations, the acceptable range of orientation changes may be zero, may be a minimal amount limited by system performance, may be less than a degree or multiple degrees or larger, based on performance conditions such as avoiding damage to a work piece or human tissue, and the like. In some cases, the acceptable range of orientation changes differ among different rotational degrees of freedom.

In some implementations, the distal portion 112 of the manipulator 102 that is maintained in position (and/or orientation) comprises only part of, or all of, a distal link of the manipulator. For example, the distal portion 112 that is maintained may comprise a distal end of the distal link, may comprise a portion of the distal link configured to be adjacent an access port during a procedure, may comprise a portion of the distal link that couples to a device that mounts to the manipulator (e.g. a device such as a tool or a cannula, etc.), may comprise the entire distal link, or may comprise the entire distal link and other more distal part(s) of the manipulator 102.

Similarly, a tool 114 or a cannula can be considered to be maintained in position (and/or orientation) when the position (and/or orientation) of a particular part of the tool 114 or cannula is maintained. In some cases, a pose of a tool 114 or a cannula is maintained by maintaining the position (and/or orientation) of a distal portion of the tool 114 or cannula, of a portion of the tool 114 or cannula adjacent to an access port, of a portion of the tool 114 or cannula that coincides with a remote center of rotation of the tool or cannula, etc.

In some examples, when the joint 106 is locked, the pose of the base 108 does not move (e.g. relative to a reference such as a reference frame anchored to the environment 10 or a reference comprising the reference point 118). If the distal portion 112 is moveable in such an instance (e.g. free and not constrained so movable relative to the reference), the controller 104 can cause movement of the distal portion 112 relative to the reference when the powered joint 116 is driven with the joint 106 locked. When the distal portion 112 supports the tool 114, the tool 114 moves with the distal portion 112, and thus moves in response to the powered joint 116 being driven. The powered joint 116 is thus drivable to move the tool 114 within a motion envelope 120 defined at least in part by the position (and/or orientation) of the base 108. The tool 114 is, for example, driven to move within the motion envelope 120 to perform an operation on target anatomy with the motion envelope 120.

In some examples, when the joint 106 is unlocked, the pose of the base 108 is movable (e.g. relative to a reference such as a reference frame anchored to the environment 10 or a reference comprising point 118). If the joint 106 is unlocked and a pose of the distal portion 112 of the manipulator 102 is maintained, the controller 104 can cause movement of the base 108 relative to the reference by driving the powered joint 116. The proximal portion 110 of the manipulator 102, for example, moves relative to the reference while the distal portion 112 of the manipulator 102 remains fixed relative to the reference. If the distal portion 112 supports the tool 114, the tool 114 does not move as a result of movement of the distal portion 112 (since the distal portion 112 has not moved as the powered joint 116 is driven). In this regard, the controller driving the powered joint 116 results in backdriving of the proximal portion 110 and hence moves the base 108; this causes motion of the base 108 relative to the distal portion 112 (or an item coupled to the manipulator, such as a cannula or the tool 114 when mounted), and relative to the reference.

The controller 104 can change the motion envelope of the tool 114 by driving the powered joint 116 while the joint 106 is unlocked and while the pose of the distal portion 112 (or an item coupled to the manipulator, such as a cannula or the tool 114 when mounted) is maintained. To adjust the position of the base 108. the controller 104 drives the powered joint 116 while the base 108 is unlocked and while a position (and/or orientation) of the distal portion 112 (or an item coupled to the manipulator) is maintained relative to a reference such as a reference comprising point 118). The base 108 moves relative to the maintained distal portion 112 (or an item coupled to the manipulator). Because the position (and/or orientation) of the distal portion 112 (or an item coupled to the manipulator) is fixed or otherwise maintained, the base 108 can be backdriven by the powered joint 116. When the base 108 moves, the motion envelope of the tool 114 can change. A similar process can be used to adjust the orientation of the base 108.

In various implementations, the controller 104 operates the powered joint 116 to move the base 108 in a manner toward achieving the desired motion envelope 122 for the tool 114. In some, implementations, the desired motion envelope 122 corresponds to a motion envelope in which the tool 114 can be driven by the manipulator 102 to reach locations appropriate for the procedure. For example, the desired motion envelope 122 can correspond to a motion envelope in which an end effector of the tool 114, or other part of the tool 114 that interacts with the workpiece or images the work site, can reach target locations for a procedure. In a medical context, the target locations may comprise target anatomy for a medical operation to be performed. In various implementations, the motion envelope is determine by the physical design, actuation limits (e.g. ranges of motion for the joints of the manipulator), pose of the manipulator 102, location of the base 108, etc.

The tool 114 is movable through the initial motion envelope 120 when the base 108 is at its initial pose depicted in FIG. 1. The tool 114 is movable through the desired motion envelope 122 when the base 108 is at a final pose (not shown in FIG. 1). The controller 104 operates the powered joint 116 to move the base 108 from its initial pose to its final pose, toward achieving the desired motion envelope 122 for the tool 114. The motion envelopes 120, 122 correspond to, for example, three-dimensional motion envelopes for the tool 114, e.g., for end effectors, a distal portion, or a distal end of the tool 114. In various implementations, the controller stops driving the powered joint 116 and/or motion of the base 108 (e.g. by actuating one or more brakes for the base 108), when the base has reached a desired location corresponding to the desired motion envelope 122 or when the desired motion envelop 122 has been achieved. In some implementations, the controller stops driving the powered joint 116 and/or motion of the base 108 before reaching the desired base location or achieving the desired motion envelope 122, in response to user commands or other criteria.

While the above example is described with respect to a manipulator and focuses on one powered joint 116, various implementations may have one or many powered joints 116. For example, in some implementations, the powered joint 116 is one of multiple powered joints 116a, 116b, 116c as shown in FIG. 1. In some implementations, the powered joints 116a, 116b, 116c are selectively driven by the controller 104 while the joint 106 is unlocked, to move the base 108 (e.g. relative to a reference such as a reference comprising the reference point 118). In the architecture shown in FIG. 1, driving the powered joint 116a with the lockable joint 106 unlocked can move the base 108 in a first degree of freedom (DOF). Meanwhile, driving the powered joint 116b with the lockable joint 106 unlocked can move the base 108 in a second DOF, and driving the powered joint 116c with the lockable joint 106 unlocked can move the base 108 in a third DOF. The first, second, and third DOFs are different DOFs. In some implementations, the controller 104 operates the powered joints (e.g. 116a, 116b, 116c) contemporaneously to move the base 108 in a manner to achieve the desired motion envelope 122 for the tool 114 (or to place the base 108 into a desired location). In some implementations, the controller 104 operates the powered joints (e.g. 116a, 116b, 116c) separately in time, or in different combinations over time, to move the base in a piecewise temporal manner to achieve the desired motion envelope 122 for the tool 114 (or to place the base 108 into a desired location).

In some implementations, one or more powered joints 116 are driven by actuators of the manipulator 102. In some implementations, one or more powered joints 116 are driven by one or more actuators, and these one or more actuators are in turn driven by an actuation module 402. In some implementations, this actuation module is removably mounted to the manipulator 102.

In the example shown in FIG. 1, one or more powered joints 116 are driven by one or more actuators of the manipulator 102, and one or more powered joints 116 are driven by one or more actuators for the actuation module 402. Specifically, the powered joints 116a, 116b are powered joints of the manipulator 102, and are driven by one or more actuators of the manipulator 102; in contrast, the powered joint 116c is a powered joint of the actuation module 402, and is driven by one or more actuators for the actuation module 402. During an operation, the controller 104 drives the powered joints 116a, 116b and moves the actuation module 402, thus moving the tool 114 relative to the base 108. Further, the controller 104 drives the powered joint 116c to rotate the tool 114 relative to the actuation module 402, and moves the tool 114 relative to the base 108.

While the above example is described with respect to a manipulator with one lockable joint 106, various implementations may have one or multiple lockable joints 106. For example, in some implementations, the lockable joint 106 is one of multiple lockable joints 106a, 106b, 106c. FIG. 1 shows such an example with three lockable joints 106a, 106b, 106c. Specifically, in the example shown in FIG. 1, the lockable joint 106a connects the manipulator 102 to a setup assembly. The lockable joint 106b connects linkages of the setup assembly. The lockable joint 106c connects the setup assembly to a support structure. In various implementations, the support structure comprises a fixture, a stand, a table or part of the table (e.g. table top, table rails, table base, table legs), etc. In some implementations, one or more of the lockable joints 106a, 106b, 106c are unlocked when the powered joint 116 is driven to reposition the base 108. In some implementations with multiple lockable joints, at least one lockable joint is locked and at least one other lockable joint is unlocked for part or the entire duration when the powered joint 116 is driven to reposition the base 108. In some implementations, selectively unlocking or locking the lockable joint 106 while driving the powered joint 116 to move the base 108 helps to guide the movement of the base 108. For example, in some implementations, motion of the base 108 toward a desired base location or desired motion envelope 122 is achieved in a piecewise manner over time. A first combination of joints 106 are locked or unlocked to facilitate a first Then, a second, different combination of joints 106 are locked or unlocked to facilitate a second motion of the base 108 toward the desired base location or desired motion envelope 122. The first and second motions of the base 108 may be in different directions. Additional combinations of locking or unlocking joints 106 may be utilized to provide additional motions of the base 108.

Although FIG. 1 shows the tool 114 being supported by the manipulator 102, and the tool 114 inserted through an access port toward the work site for a workpiece 109, the techniques discussed can also be used to reposition the base of a system without a tool 114, or with a tool 114 that is mounted for a procedure on a work site accessed without an access port, or with a tool 114 that is mounted but not inserted into an access port for accessing the work site. For example, the distal portion 112 of the manipulator 102 (or an item held in the distal portion 112, such as a cannula or a tool 114) may be externally maintained in position and/or orientation by any appropriate technique.

Example external maintenance techniques include any one or combination of: operator applied forces, fixtures, other robotic arms, access port wall forces (e.g. patient tissue forces where the work piece comprises patient anatomy) and other techniques different from driving the actuators or brakes of the manipulator 102. Thus, the position (and/or orientation) of the distal portion 112 can be maintained directly, or indirectly through an intermediary such as an item mounted to the distal portion 112. As a specific example, in some implementations, a pose of the distal portion 112 may be externally maintained by maintaining a position of the tool 114 when coupled to the distal portion 112 or another portion of the manipulator 102, or of a cannula or other device coupled to the distal portion 112 or another portion of the manipulator 102.

Figure 2:
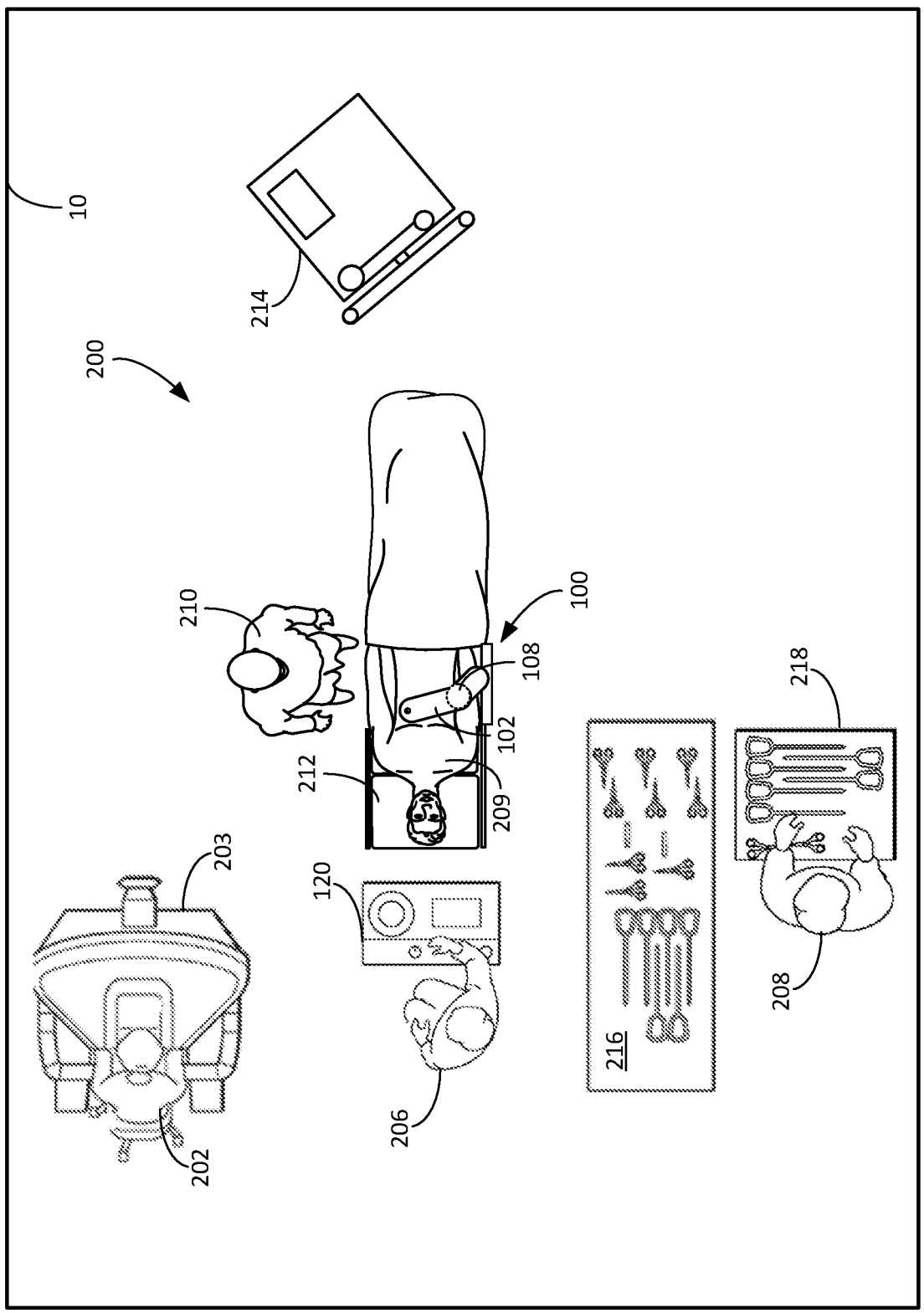
FIG. 2 is a top view of an example surgical system.

FIG. 2 shows an example computer-assisted system comprising a surgical system 200. In this example, a surgeon 202 remote from the patient 209 performs a remote surgical operation by manipulating control inputs of a console 203 located remotely from the manipulator 102. In some implementations, as shown in FIG. 2, the environment 10 includes obstacles, e.g., operators 206, 208, 210, an operation table 212, an electronics cart 214, surgical tool tables 216, 218, and other objects in the environment 10. During operation of the manipulator 102, the manipulator 102 may collide with an obstacle as the tool 114 is moved through its motion envelope. As described herein, to inhibit collision with an obstacle, the position (and/or orientation) of the base 108 of the manipulator 102 is adjusted to achieve a desired motion envelope based on a likelihood of collision between the manipulator 102 and the obstacle. In particular, the motion envelope of the tool 114 (shown in FIG. 1) is adjusted to inhibit the likelihood of collision, e.g., the likelihood of collision when the tool 114 is moved through the desired motion envelope is less than the likelihood of collision when the tool 114 is moved through its initial motion envelope. This adjustment may be performed intraoperatively, defined at initial setup by using an estimate of collision probability when defining a desired motion envelope 122, etc.

Figure 3:
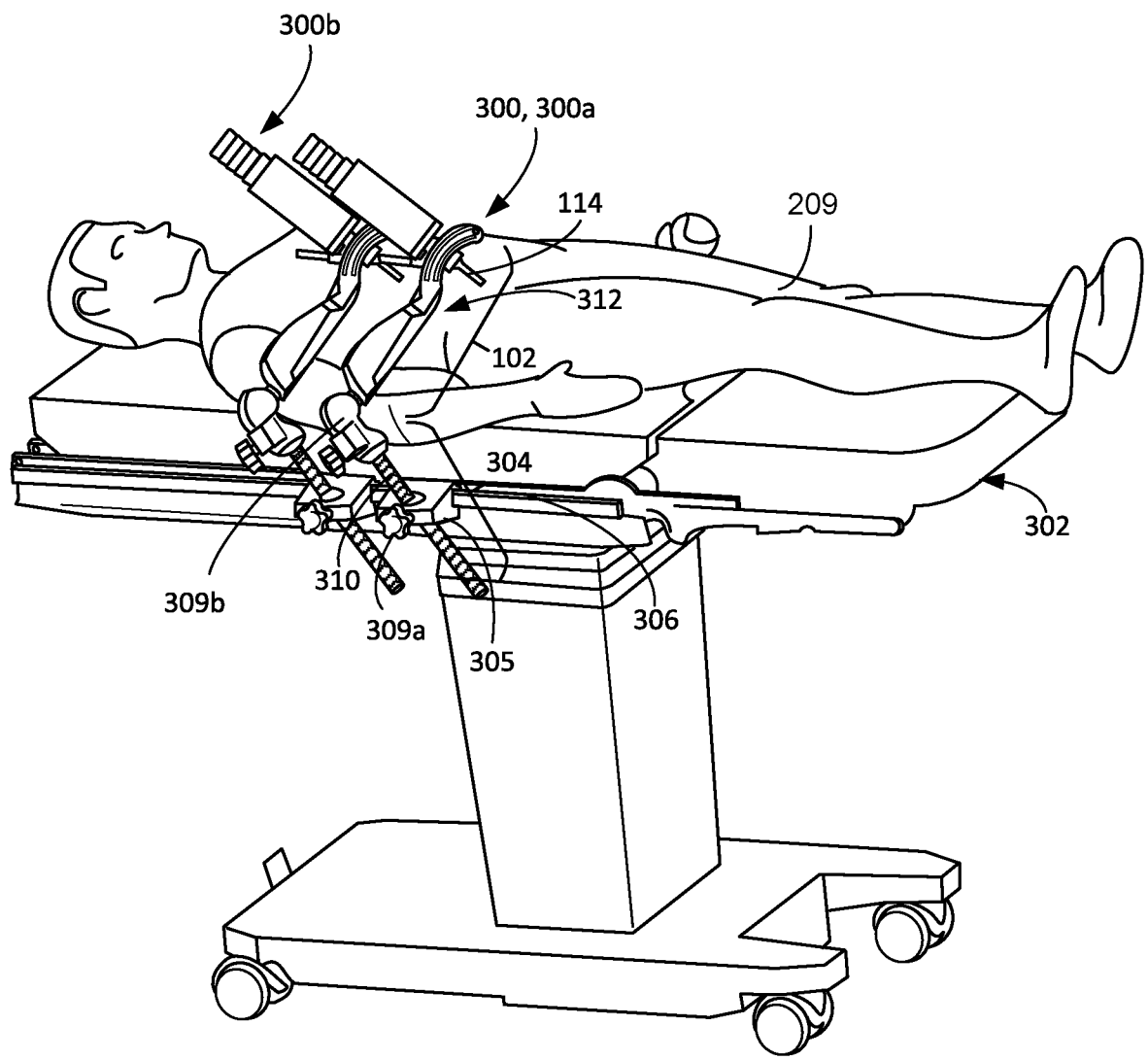
FIG. 3 is a perspective view of an example surgical environment including first and second remotely controllable manipulators.

FIG. 3 is a perspective view of an example surgical environment including first and second remotely controllable manipulators. FIG. 3 is perspective view of the patient 209 on an operating table 302. A manipulator system 300 includes a setup assembly 304 that supports the manipulator 102 relative to a reference (e.g., a reference comprising the reference point 118) described with respect to FIG. 1. The setup assembly 304 is mounted to a support structure 306. In some implementations, the support structure 306 is part of the operating table 302, e.g., is a bed rail of the operating table 302. The support structure 306 includes a bracket 305 that fixes the setup assembly 304 to the operating table 302. In some examples, the setup assembly 304 and/or the manipulator 102 are manually adjusted, e.g., by a human operator, to a desired pose relative to the reference point. The reference point is fixed relative to the support structure 306. The desired pose can be selected from one of a multitude of selectable poses relative to the patient 209. The desired pose, for example, corresponds to a pose in which an insertion axis of the tool 114 is aligned with a location of an access port through the patient body wall 20. The operator manually manipulates the setup assembly 304 and/or the manipulator 102 to enable the tool 114 to access target anatomy through the access port.

While the setup assembly 304 is described as being rail-mounted, in some implementations, the setup assembly 304 is mounted such that the setup assembly 304 extends from an overhead frame, a floor, or other fixed portion of the surgical environment. The setup assembly 304, for example, extends from a cart movable relative a floor of the surgical environment, and the cart includes a braking mechanism to maintain a position (and/or orientation) of the cart relative to the floor. The setup assembly 304, for example, is mounted to a gantry movable relative to an overhead frame. The gantry moves relative to the overhead frame to reposition the setup assembly 304 relative to the patient.

The manipulator 102 is releasably and adjustably coupled to the setup assembly 304. The base 108 of the manipulator 102, e.g., the proximal end of the manipulator 102, is mounted to a distal portion of the setup assembly 304. The setup assembly 304 includes a setup joint system that couples the support structure 306, the setup assembly 304, and the manipulator 102. The joint system is selectively lockable to inhibit or allow relative motion between the support structure 306 and the setup assembly 304 and/or between the manipulator 102 and the setup assembly 304. The setup joints of the setup assembly 304 are manually adjustable. The setup assembly 304 has multiple degrees of freedom (DOFs), and is fixed stationary in a desired configuration when the joint system is locked.

The joint system includes one or more lockable setup joints. In some examples, the joint system includes lockable joints 309a, 309b, with the lockable joint 309a being configured to be locked to fix the setup assembly 304 relative to the support structure 306, and the lockable joint 309b being configured to be locked to fix the setup assembly 304 to the manipulator 102. The lockable joints 309a, 309b can be passive (manually adjustable) or active (power adjustable or power-assist adjustable). In the example depicted in FIG. 3, the lockable joints 309a, 309b are manually adjustable and manually lockable.

In some implementations, one or more of the lockable joints 309a, 309b are manually lockable joints. The operator manually operates a manually operable mechanism, e.g., a knob, a lever, a switch, a button, etc., to lock a lockable joint. The manually operable mechanism, in some cases, is a purely mechanical mechanism that is manually locked to inhibit relative motion of components of the manipulator system 300. In some cases, an electrical signal initiating a locking operation is generated when the manually operable mechanism is manually operated by the operator. The electrical signal causes the electromechanical mechanism to lock a lockable joint. In some cases, the controller 104 is configured to operate the electromechanical mechanism. The electrical signal initiating the locking operation causes the controller 104 to operate the electromechanical mechanism to lock the lockable joint. In this regard, the controller 104 is also configured to identify when the lockable joint is unlocked or when the lockable joint is locked. In some cases, the lockable joints 309a, 309b include a hydraulic locking mechanism or other mechanism to assist in locking the lockable joints 309a, 309b. A number of alternatives to this locking behavior are possible. In some cases, the lock is by default "always on," and the electrical signal initiates an unlocking operation when the manually operable mechanism is manually operated by the operator or when the controller 104 provides signals for causing such unlocking. Or, the lock is by default "always on," and the electrical signal initiates an unlocking operation when the manually operable mechanism is not manually operated by the operator, or when the controller 104 provides signals for locking or is not providing signals for unlocking.

In the example shown, a linkage 310 of the setup assembly 304 is fixed to a linkage assembly 312 of the manipulator 102 when the lockable joint 309b fixes the setup assembly 304 to the manipulator 102. In particular, a distal portion of the linkage 310 is fixed to a proximal portion of the linkage assembly 312 through the lockable joint 309b when the lockable joint 309b is locked. The proximal portion of the linkage 310 is mounted to the support structure 306 through the lockable joint 309a. As described with respect to FIGS. 4A to 4C, the linkage assembly 312 includes one or more linkages that, when driven through one or more powered joints, move so as to cause relative repositioning of the base 108, the distal portion 112, and/or the an item coupled to the manipulator 102 such as tool 114. The linkage assembly 312, for example, enables yaw and pitch motion of the tool 114.

In some implementations, one of the lockable joints 309a, 309b corresponds to the lockable joint 106 described with respect to FIG. 1. If the manipulator system 300 is mounted to the support structure 306, and the tool 114 is mounted to the manipulator system 300, the tool 114 moves relative to the support structure 306 when the powered joint 116 is driven and when one or more of the lockable joints 309a, 309b are locked. For example, the lockable joint 309a, when locked, inhibits motion of the setup assembly 304 relative to the support structure 306 by inhibiting motion of the linkage 310 of the setup assembly 304 relative to the support structure 306. The lockable joint 309b, when locked, inhibits motion of the setup assembly 304 relative to the manipulator 102 by inhibiting motion of the linkage 310 of the setup assembly 304 relative to the linkage assembly 312 of the manipulator 102. In this regard, when the lockable joint 309a is unlocked, the base 108 of the manipulator 102 is movable relative to the support structure 306, e.g., due to movement of the linkage 310 relative to the support structure 306. When the lockable joint 309b is unlocked, the base 108 of the manipulator 102 is movable relative to the support structure 306, e.g., due to movement of the linkage assembly 312 relative to the linkage 310.

When one or both of the lockable joints 309a, 309b are unlocked and the pose of the tool 114 is maintained, the base 108 is repositioned with respect to the tool 114 (or where the tool 114 would be if mounted to the manipulator 102) when the powered joint 116 is driven, thereby changing the motion envelope of the tool 114. The base 108 is backdriven by the powered joint 116 so that the proximal portion 110 of the manipulator 102 is moved instead of the distal portion 112 of the manipulator 102. The torque input at the powered joint 116 generates output movement at the base 108 rather than at the distal portion 112.

In this example, to move the tool 114 relative to the support structure 306, the powered joint 116 is driven with the joint system locked, e.g., with both the lockable joints 309a, 309b locked. As described herein with respect to FIGS. 4A-4C, in some implementations, multiple powered joints are driven with the lockable joints 309a, 309b locked to move the tool 114 relative to the support structure 306. As described herein, the powered joints can be powered joints of the manipulator 102 and/or powered joints of the actuation module 402.

In some implementations, the manipulator system 300 is one of multiple manipulator systems 300a, 300b, where each manipulator system 300a, 300b includes a corresponding setup assembly and a corresponding remotely controllable manipulator. Both manipulator systems 300a, 300b are mounted to the support structure 306. In some examples, multiple tools are used for a procedure. As a surgical example, multiple surgical tools are often used for a single surgical operation.

As further surgical examples, a variety of alternative computer-assisted tele-operated surgical tools of different types and differing end effectors may be used in conjunction with the techniques described herein. In some cases, the surgical tools of at least some of the manipulators are removed and replaced during a surgical procedure. In some cases, the computer-assisted tele-operated surgical tools include multiple DOFs such as, but not limited to, roll, pitch, yaw, insertion depth, opening/closing of jaws, actuation of staple delivery, activation of electro-cautery, and the like. At least some of such DOFs can be actuated by actuators of the manipulator 102 to which the surgical tool selectively coupled. Several of the end effectors, including, for example, DeBakey Forceps, microforceps, and Potts scissors include first and second end effector elements that pivot relative to each other so as to define a pair of end effector jaws. Other end effectors, including scalpels and electrocautery probes, have a single end effector element. For surgical tools having end effector jaws, the jaws will often be actuated by squeezing the grip members of input devices. In some cases, the surgical tool includes an image capture device, such as a camera.

Figure 4A:
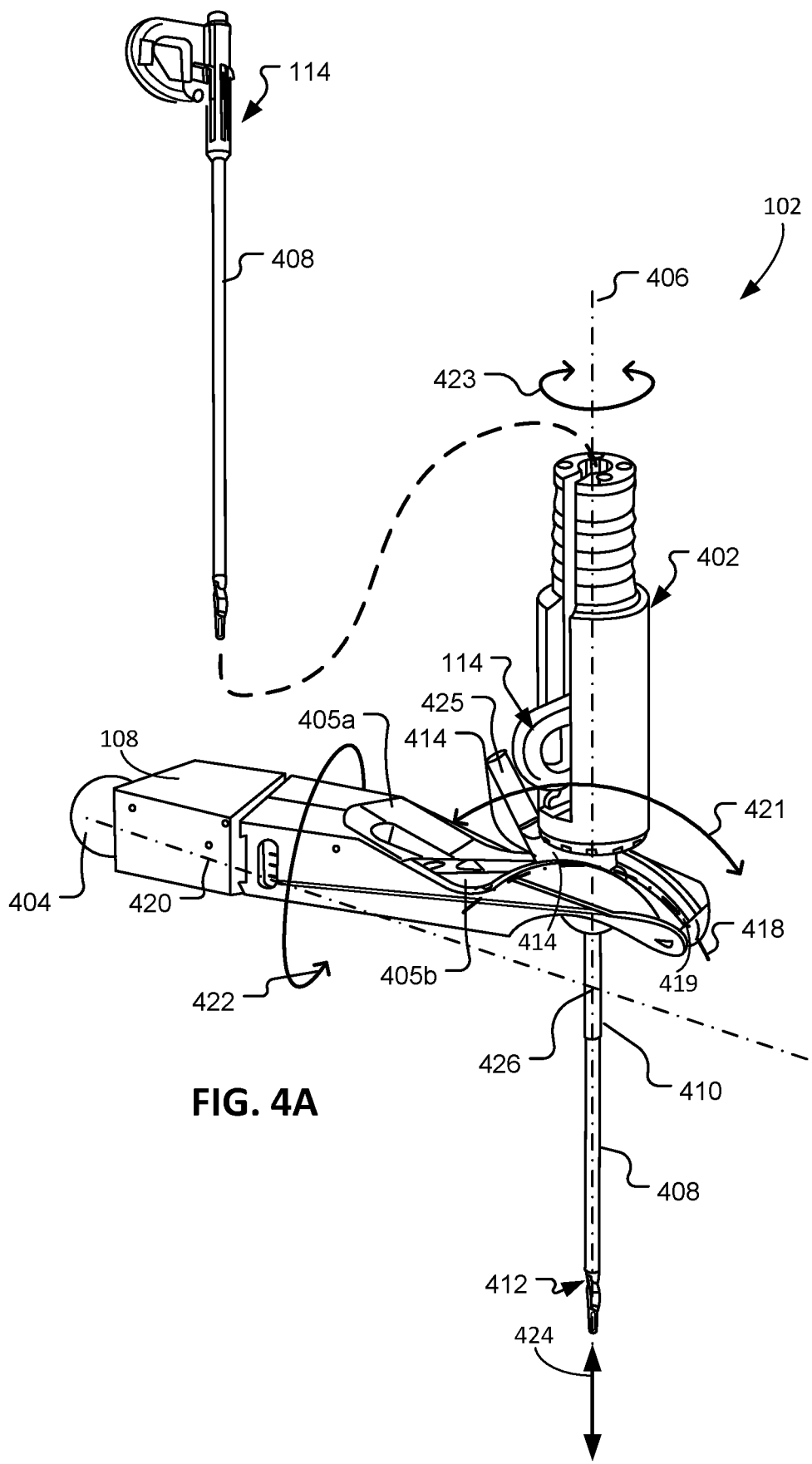
FIG. 4A is a side perspective view of an example manipulator that can be coupled to a setup assembly.

FIG. 4A depicts a perspective view of an example of the manipulator 102 and the tool 114 to be mounted to the manipulator 102. The manipulator 102 may be coupled to a setup assembly such as setup assembly 304. The manipulator 102 includes, for example, a mount 404 on the base 108 to releasably couple the setup assembly 304 to the manipulator 102.

The base 108 is configured to releasably couple with the setup assembly 304. The base 108 includes, for example, the mount 404. The mount 404 couples the base 108 to the setup assembly 304 such that the base 108 is movable relative to the setup assembly 304 in three or more degrees of freedom. The mount 404 is, for example, a ball extending from a proximal end of the base 108, the ball being configured to be received in a socket of the setup assembly 304. The mount 404 allows for the manipulator 102 to be coupled to the setup assembly 304 in a manner such that the manipulator 102 can be reoriented relative to the setup assembly 304. The mount 404 corresponds to, for example, the lockable joint 309b described with respect to FIG. 3. When a desired orientation between the manipulator 102 and the setup assembly 304 has been attained, the mount 404 between can be releasably locked in a fixed orientation, e.g., the lockable joint 309b is locked. The base 108 then remains stationary relative to the setup assembly 304 until the mount 404 is unlocked.

As described herein, the distal portion 112 of the manipulator 102 is configured to be coupled to the tool 114. The manipulator 102 includes an actuation module coupling 414 to releasably couple with an actuation module 402 to which the tool 114 is mounted. In a surgical example, the actuation module 402 comprises a surgical tool actuation module for actuating tools 114 that comprise surgical tools. The coupling 414 is configured to releasably couple with cannula 410 that is coaxial with an insertion axis 406 of the tool 114. The cannula 410 defines a lumen that slidably receives a shaft 408 of the tool 114 (or of other devices such as, but not limited to, an endoscope) along the insertion axis 406. For a surgical operation, the cannula 410 may comprise a patient body wall access configured to extend distally from the coupling 414 through the patient via a surgical access location on the patient body wall.

The actuation module 402 releasably receives the tool 114. The actuation module 402 is, for example, detachable from the manipulator 102 to enable the actuation module 402 to be easily interchanged with another actuator system. When the tool 114 is mounted to the actuation module 402, the shaft 408 of the tool 114 extends through the cannula 410. In a surgical example, the cannula 410 extends through the patient body wall to guide the shaft 408 and an end effector 412 of the tool 114 through the patient body wall into a cavity where the end effector 412 is to perform the surgical operation. The end effector 412 is remotely controlled by the surgeon 202 (shown in FIG. 2) when the computer-assisted tele-operated surgery is performed.

The actuation module 402 is, for example, a standalone unit including a system of actuators to control motion of the tool 114 when the tool 114 is mounted to the actuation module 402. The manipulator 102 drives the coupling 414 to control motion of the actuation module 402 and the tool 114 mounted to the actuation module 402. The linkage assembly 312 of the manipulator 102 is, for example, releasably coupled with the actuation module 402 through the coupling 414 so that the actuation module 402 moves when the linkage assembly 312 is operated.

Referring also to FIGS. 4B and 4C, the manipulator 102 includes the linkages 405a, 405b, e.g., of the linkage assembly 312. The base 108 and the linkage 405a are rotatably coupled, e.g., the linkage 405a is rotatable relative to the base 108. A proximal portion of the linkage 405b is coupled to an actuator of the manipulator 102, e.g., positioned within the linkage 405a. A distal portion of the linkage 405b is coupled to the coupling 414.

In some examples, the manipulator 102 includes actuators to control a first set of DOFs of the tool 114, and the actuation module 402 includes one or more actuators to control a second set of DOFs of the tool 114. The first set of DOFs include, for example, a pitch motion 421, a yaw motion 422, and a roll motion 423 of the tool 114 relative to a reference (e.g., a reference comprising the reference point 118). The tool 114 is configured to undergo the pitch motion 421, the yaw motion 422, and the roll motion 423 when the tool 114 is mounted to the actuation module 402 and the actuation module 402 is mounted to the coupling 414. The second set of DOFs of the tool 114 include, for example, an insertion motion 424 of the tool 114. In some examples, if the end effector 412 of the tool 114 includes a DOF, the second set of DOFs further includes an end effector motion of the end effector 412.

The controller 104 of the manipulator 102 is configured to actuate the pitch motion 421, the yaw motion 422, and the roll motion 423 of the coupling 414 in response to input, e.g., an input from the surgeon 202 using the surgeon console 203 as described in reference to FIG. 2. The manipulator 102 includes two selectively operable actuators to actuate the pitch motion 421 and the yaw motion 422, respectively. In some implementations, the manipulator 102 includes three or more selectively operable actuators. The actuation module 402 includes a selectively operable actuator to actuate the roll motion 423. In some cases, the actuation module 402 is an integral component of the manipulator 102, and the manipulator 102 includes the actuator to actuate the roll motion 423. In some implementations, one of the actuators for the pitch motion 421, the yaw motion 422, and the roll motion 423 corresponds to an actuator of the powered joint 116 described with respect to FIG. 1. The actuators for the pitch motion 421, the yaw motion 422, and the roll motion 423 are, for example, electric motors.

For the pitch motion 421, the coupling 414 is translated along a path 418 through a slot 419 in the linkage 405a when an actuator (not shown) of the manipulator 102 is driven. The linkage 405a and the linkage 405b are coupled such that the linkage 405b is movable relative to the linkage 405a along the path 418 through the slot 419 in the linkage 405a. The coupling 414 is driven, e.g., translate along the path 418 when the actuator drives the linkage 405b. The path 418 corresponds to, for example, an arcuate path along which a distal portion of the linkage 405b travels, and the arcuate path defines a pitch arc.

For the yaw motion 422, the linkage 405a is rotated relative to the base 108 about a yaw axis 420 when another actuator (not shown) of the manipulator 102 is driven. The linkage 405a is, for example, rotatable about the yaw axis 420 in a counterclockwise direction and/or a clockwise direction. The linkage 405b and the coupling 414 are rotationally coupled to the linkage 405a such that the linkage 405b and the coupling 414 rotate with rotation of the linkage 405a.

For the roll motion 423, the controller 104 of the manipulator 102 is operable to drive the actuation module 402 to rotate the actuation module 402 relative to the coupling 414. In some examples, the actuation module 402 with the tool 114 rotates when a gear fixed to the actuation module 402 is driven. The manipulator 102 includes, for example, an actuator 425 operable by the controller 104 to rotate the actuation module 402 about the insertion axis 406.

When the controller 104 is connected to the actuation module 402, e.g., electrically connected to the actuation module 402, the controller 104 is configured to operate actuators of the actuation module 402. The actuators of the actuation module 402 is operable to cause the insertion motion 424 of the tool 114 and to actuate the end effector 412 of the tool 114. In particular, the controller 104 in response to input, e.g., an input from the surgeon 202 using the surgeon console 203 as described in reference to FIG. 2, generates control signals to operate the actuators of the actuation module 402. In this regard, in some examples, the manipulator 102 does not include an actuator to cause actuation of the insertion motion 424 or to actuate the end effector 412. Rather, the actuation module 402 includes these actuators, and these actuation module 402 can be disconnected from the controller 104 to enable different actuation modules to be easily mounted to the manipulator 102.

In some examples, to actuate the insertion motion 424 when the actuation module 402 is mounted to the manipulator 102, the controller 104 operates an actuator of the actuation module 402 to insert the tool 114 into the patient. The actuator for the insertion motion 424 is, for example, an electric motor housed in the actuation module 402. The tool 114 undergoing the insertion motion 424 translates through patient body tissue along the insertion axis 406. The actuation module 402 is also operable to retract the tool 114 from the patient, e.g., translate the tool 114 away from the patient body tissue along the insertion axis 406.

The actuation module 402 is, in some cases, operable to actuate the end effector 412 of the tool 114. If the end effector 412 includes movable or pivotable elements, the actuation module 402 is operable to actuate the end effector 412 to cause end effector motion, e.g., to cause the end effector elements to move or pivot. If the end effector 412 includes an electrocautery device, the actuation module 402 is operable to deliver electrical energy to the electrocautery device to cauterize patient tissue. As described herein, the tool 114 may include other types of end effectors, and the actuation module 402 can accordingly include other actuation systems to operate the end effectors. The actuator for the end effector actuation depends on the type of the end effector 412. If the end effector 412 includes movable end effector elements, the actuator is an electric motor. If the end effector 412 delivers electrical energy, the actuator is a variable power source operable to deliver electric energy to the patient tissue.

In some implementations, the manipulator 102 is a hardware-constrained remote center of motion system. The base 108 and the linkages 405a, 405b are arranged relative to one another such that the insertion axis 406 and the yaw axis 420 intersect each other at a center point of the arcuate path 418, e.g., at a remote center of motion 426.

The remote center of motion 426 is a point in space around which the pitch motion 421, the yaw motion 422, and the roll motion 423 described herein are made. For example, when the tool 114 undergoes the pitch motion 421, the position of the remote center of motion 426 is unchanged because the center point of the arcuate path 418 is located at the remote center of motion 426. The center point of the radius of the arcuate path 418 is, for example, coincident with the remote center of motion 426. Hence, the pitch motion 421 of the tool 114 is made about the remote center of motion 426 because the center point of the radius of the arcuate path 418 is coincident with the remote center of motion 426.

In some examples, as the linkage 405a is rotated in relation to the base 108 to generate the yaw motion 422 of the tool 114, the position of the remote center of motion 426 is unchanged because the yaw axis 420 passes through the remote center of motion 426. Furthermore, as the actuation module 402 is rotated in relation to the linkage 405b about the insertion axis 406 to generate the roll motion 423 of the tool 114, the position of the remote center of motion 426 is unchanged because the insertion axis 406 passes through the remote center of motion 426.

In some implementations, at all positions of the coupling 414 along the arcuate path 418, the insertion axis 406 and the yaw axis 420 intersect each other at the center of the arcuate path 418 where the remote center of motion 426 is located. Alternatively or additionally, at all positions of the coupling 414 about the yaw axis 420 of the linkage 405a relative to the base 108, the insertion axis 406 and the yaw axis 420 intersect each other at the center of the arcuate path 418 where the remote center of motion 426 is located. Further, at all positions of the coupling 414 along the arcuate path 418 in combination with any position about the yaw axis 420 of the linkage 405a relative to the base 108, the insertion axis 406 and the yaw axis 420 intersect each other at the center of the arcuate path 418 where the remote center of motion 426 is located. In this regard, the motion envelope 120 of the tool 114 described with respect to FIG. 1 depends on the location of the remote center of motion 426. The motion envelope 120, for example, includes all possible positions of a portion of the tool 114 (such as the end effector of the tool 114) as the tool 114 undergoes the pitch motion 421, the yaw motion 422, and the roll motion 423 at a given position of the remote center of motion 426. In some implementations, the remote center of motion 426 is located at other points, e.g., at a particular distance away from the insertion axis 406. In some implementations, the manipulator 102 is implemented using a software-constrained remote center of motion rather than, or in addition to, a remote center of motion 426.

During an operation such as a surgical operation, the remote center of motion 426 is positioned, in some cases, coincident with a region of the cannula 410. The remote center of motion 426 is, for example, positioned at the body wall of the patient. One advantage of such an arrangement is that while the tool 114 undergoes the pitch motion 421, the yaw motion 422, and/or the roll motion 423, any resulting stress applied to the body wall by the cannula 410 is negligible because the portion of the cannula 410 that interfaces with the body wall, i.e., at the remote center of motion 426, remains substantially stationary even while the tool 114 undergoes the motions 421, 422, and 423.

Figure 5:
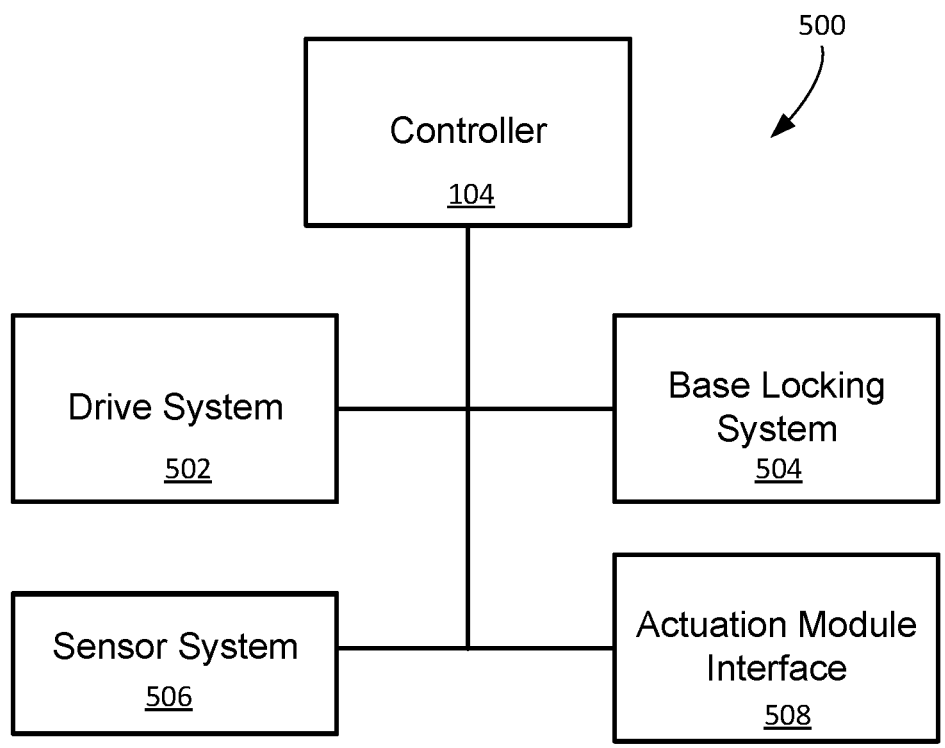
FIG. 5 is a block diagram of an example computer-assisted system.

FIG. 5 presents a block diagram of an example control system 500 that can be used with a computer-assisted system such as the relocation system 100. As shown in FIG. 5, the control system 500 includes the controller 104 and a drive system 502. The controller 104 can operate the drive system 502 in a manner to cause relative motion of the distal portion 112 of the manipulator 102 and the base 108. The drive system 502 includes the powered joint 116 described with respect to FIG. 1. The powered joint 116, for example, corresponds to a joint for one of the actuators for the pitch motion 421, the yaw motion 422, and/or the roll motion 423. The powered joint 116 can be operated to actuate the pitch motion 421, the yaw motion 422, and/or the roll motion 423 of the tool 114 and can also be operated to actuate motion of the base 108, e.g., to translate the base 108 in space. If the drive system 502 includes multiple powered joints to back-drive the base 108, the base 108 can be movable in two or more dimensions. The drive system 502 includes, for example, one or more of the actuators described herein to drive the linkage assembly 312.

In some implementations, the control system 500 includes a base locking system 504. The controller 104 can operate the base locking system 504 in a manner to selectively fix motion of the base 108 relative to a reference (e.g., a reference comprising the reference point 118). The base locking system 504 includes, for example, a passive or powered joint that is lockable to fix relative positions (and/or orientation)s of linkages connected at the joint. The base locking system 504 includes, for instance, the lockable joints 309a, 309b. In some cases, the controller 104 operates the base locking system 504 to selectively unlock a joint to enable relative motion of linkages connected at the joint. Alternatively, rather than being operated by the controller 104, the base locking system 504 is operated by a human operator. A joint of the base locking system 504 includes, for instance, a manually operable locking device, e.g., a knob, a screw, etc., that, when manually operated, fixes relative motion of linkages connected at the joint to lock the joint. The manually locking device is also manually operable to unlock the joint, thereby enabling relative motion of linkages connected at the joint.

In some implementations, the control system 500 includes a sensor system 506. The sensor system 506 includes one or more sensors to detect treatment parameters and conditions of equipment in the computer-assisted system (e.g. the surgical system 200). In some examples, the manipulator 102 includes a pose sensor positioned at the powered joint 116 to detect relative poses of the linkages connected at the powered joint 116. The pose sensor can include a pressure sensor, torque sensor, force sensor, position sensor, velocity sensor, accelerometer, rotary encoder, linear encoder, and/or other appropriate sensors to determine the position(s) and/or orientation(s) of linkages associated with the powered joint. The controller 104, in some cases, determines a pose of the base 108 based on a signal from the pose sensor. In some cases, the sensor system 506 includes a pose sensor associated with the base 108.

In some examples, the sensor system 506 includes an obstacle detection sensor. The obstacle detection sensor is positioned at one or more locations in the relocation system 100 to detect imminent collision or contact with nearby obstacles in the environment 10. The manipulator 102, for instance, includes an obstacle detection sensor to detect when the manipulator 102 contacts or nearly contacts nearby obstacles. The obstacles can include other equipment of the computer-assisted system (e.g. the surgical system 200), operators within the environment 10, or other objects within the environment 10. The obstacle detection sensor is, for example, a contact sensor, proximity sensor, optical time-of-flight sensor, or other sensor appropriate for detecting contact with an obstacle or a distance of an obstacle. The obstacle detection sensor can also include, for example, tape switches, flexible sensing arrays, individual force sensing resistors or force sensing resistor arrays, or passive capacitive sensing systems.

The control system 500 further includes an actuation module interface 508 that enables the actuation module 402 to electrically interface with the controller 104 when the actuation module 402 is mounted to the coupling 414. When the actuation module 402 interfaces with the controller 104 through the actuation module interface 508, the controller 104 is capable of operating the actuators of the actuation module 402 to effect the insertion motion 424 and the end effector actuation, as described herein.

Figure 6:
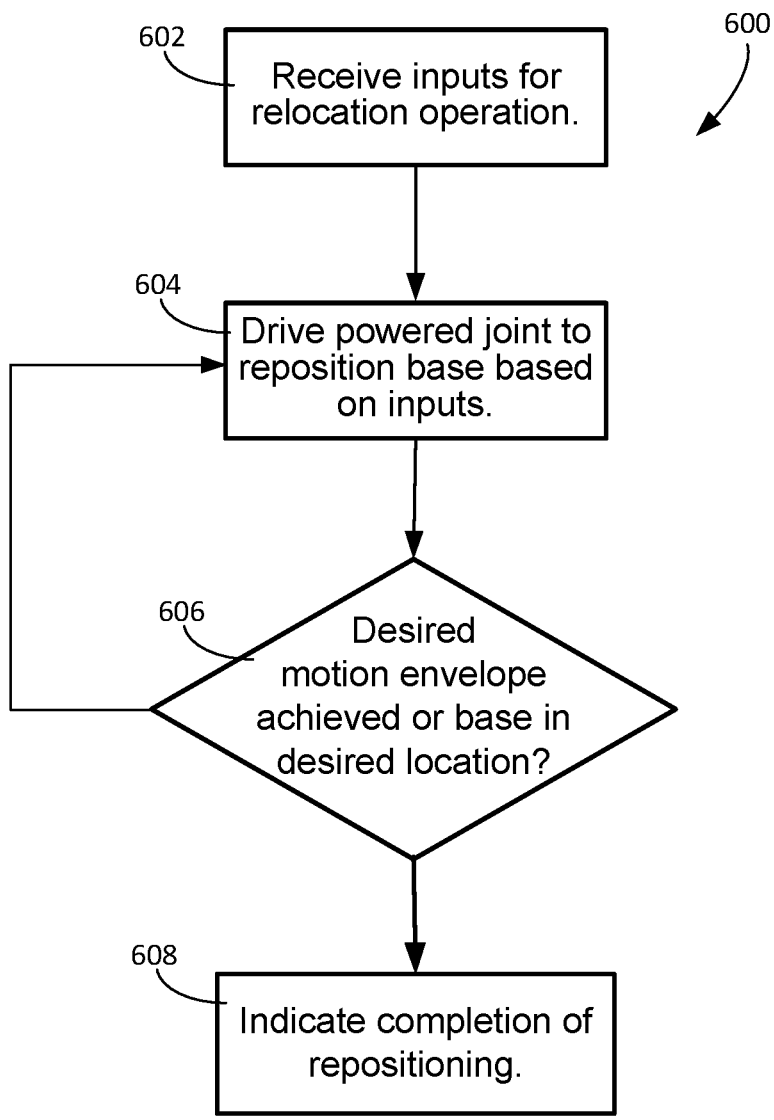
FIG. 6 is a flowchart of an example process of relocating a manipulator.

The control system 500 is operable to reposition the base 108 of the manipulator 102 by operating the powered joint 116 to backdrive the base 108. Example processes and operations to drive the powered joint 116 to position the base 108 while maintaining the position (and/or orientation) of the distal portion 112 (and/or an item coupled to the manipulator 102 such as a cannula or the tool 114) are described herein. FIG. 6, for instance, depicts a flow chart of an example process 600 of relocating a manipulator such as manipulator 102. For example, the process 600 can be used to control the powered joint 116 to backdrive the base 108. Operations of the process 600 are, for example, performed by the controller 104.

Figure 7A:
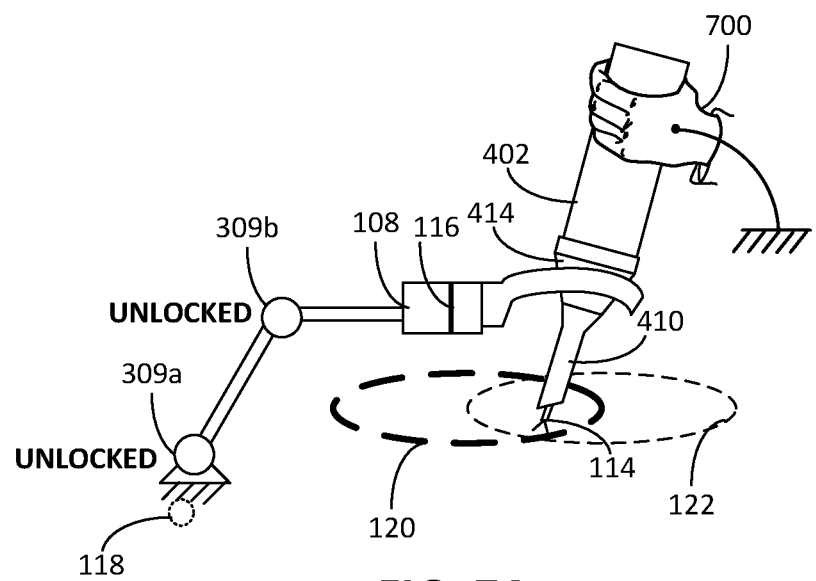
FIGS. 7A and 7B depict an example process of relocating a manipulator.
Figure 7B:
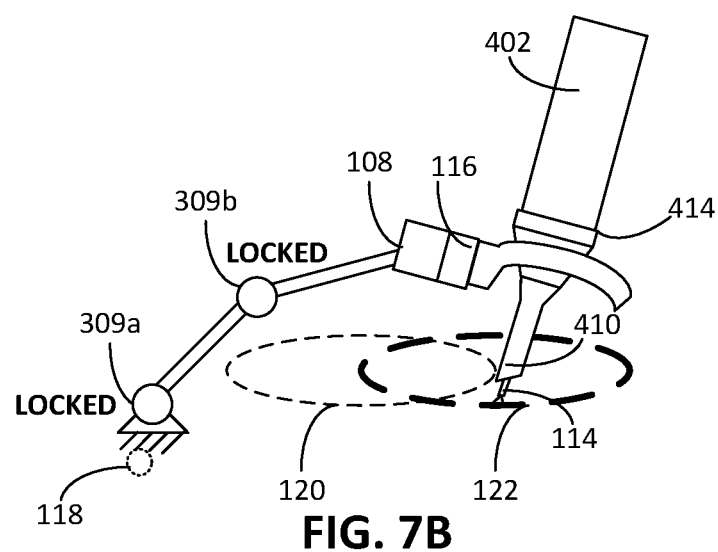

FIGS. 7A and 7B depict a specific example in which a process such as the process 600 is executed to optimize the motion envelope of the tool 114. The manipulator 102 is operated to move the base 108 from a position (and/or orientation) in which the tool 114 has the initial motion envelope 120 (FIG. 7A) to a position (and/or orientation) in which the tool 114 has the desired motion envelope 122 (FIG. 7B).

The desired motion envelope 122 enables the tool 114 to more easily reach a target portion of the anatomy. In some examples, the process 600 is initiated near a beginning of a procedure, (e.g., in a surgical example, before the powered joint 116 has been operated to perform surgery on anatomy of the patient 209). In some examples, the process 600 is initiated during a procedure, (e.g., in a surgical example, after the controller 104 has operated the powered joint 116 for a period of time to perform surgery on anatomy of the patient 209 using the tool 114). The tool 114 is movable through the initial motion envelope 120 (FIG. 7A) during a first portion of the procedure, and the tool 114 is movable through the desired motion envelope 122 (FIG. 7B) through a second portion of the procedure. The process 600 is initiated after the first portion of the procedure and before the second portion of the procedure. In a surgical example, in the first portion of the surgical procedure, surgery is performed on a first part of the anatomy of the patient 209, and in the second portion of the surgical procedure, surgery is performed on a second part of the anatomy of the patient 209. The initial motion envelope 120 for the tool 114 can enable the tool 114 to more easily reach the first part of the anatomy, whereas the desired motion envelope 122 for the tool 114 can enable the tool 114 to more easily reach the second part of the anatomy.

During or before the process 600, one or more lockable joints, e.g., the lockable joints 309a, 309b, are unlocked to enable the base 108 to be manually moved relative to a reference (e.g., a reference comprising the reference point 118). The lockable joints 309a, 309b, when unlocked, enable motion of the manipulator 102 and hence motion of the actuation module 402 and the tool 114. In some examples, while the lockable joints 309a, 309b are unlocked, the human operator 700 manipulates the lockable joints 309a, 309b to reposition the base 108, a portion of the manipulator 102 such as the distal portion 112, and/or an item coupled to the manipulator 102 such as a cannula or the tool 114. The operator 700, for example, manually grasps the actuation module 402 and/or the tool 114 and directs the tool 114 toward target anatomy of the patient 209. In particular, the actuation module 402 is manipulated so that the insertion axis of the tool 114 is directed toward the target anatomy.

The desired motion envelope 122, in this regard, is defined in part by the position (and/or orientation) of the tool 114 after the manual manipulation. To achieve the desired motion envelope 122 after the manual manipulation, the controller 104, for example, executes the process 600 depicted in FIG. 6.

At an operation 602 of the process 600, the controller 104 determines the desired motion envelope 122 based on input data received by the controller 104. The input data include, in some cases, instructions to initiate the operation 602 and data used to determine the manner in which the powered joint 116 should be driven. The input data correspond to data usable by the controller 104 to determine a desired motion envelope, e.g., the desired motion envelope 122, for the tool 114. Example types of input data include: a motion envelope or a range of motion of a setup joint for the manipulator, a type of operation to be performed, a likelihood of collision of the manipulator (such as with a person, a table, another manipulator), a pose of a second manipulator of the computer-assisted system, a pointing direction of the tool 114 (e.g. after manual manipulation to point at a target such as a portion of an industrial workpiece or target anatomy), etc. In some examples, based on the input data, the controller 104 determines the desired motion envelope 122 to be a motion envelope in which the tool 114 is centered within a range of motion of each of its DOFs. The tool 114 is, for example, centered within the roll range of motion, pitch range of motion, and roll range of motion.

In alternative or additional examples, the manipulator 102 is not optimally configured when the tool 114 is centered. The controller 104 determines a desired motion envelope 122 in which the tool 114 is not centered, e.g., biased from the center of the range of motion of each its DOFs, to improve performance of the manipulator 102 and the tool 114. The controller 104 receives the input data and determines the desired motion envelope 122 to be a motion envelope in which the tool 114 is biased based on the input data. Examples of input data usable by the controller 104 to determine a desired motion envelope are described herein with respect to FIG. 8.

At an operation 604, the controller 104 drives the powered joint 116 to reposition the base 108 based on the input data received at the operation 602. Referring to FIG. 7A, during the operation 604, the base 108 is repositioned relative to a reference (e.g., a reference comprising the reference point 118) and relative to the tool 114. The controller 104, for example, generates control signals, and transmits the control signals to cause the drive system 502 to drive the powered joint 116. The motion envelope of the tool 114 changes as the position (and/or orientation) of the base 108 relative to the tool 114 changes. In particular, when the relocation system 100 is in a first configuration shown in FIG. 7A, the tool 114 has the initial motion envelope 120. When the relocation system 100 is a second configuration shown in FIG. 7B, the tool 114 has the desired motion envelope 120. The controller 104 generates the control signals to achieve the desired motion envelope 122 for the tool 114 when the powered joint 116 is driven.

As shown in FIG. 7A, the controller 104 drives the powered joint 116 while the lockable joints 309*a*, 309*b* are unlocked. To unlock the lockable joints 309*a*, 309*b*, In some examples, an operator 700 manually operates the lockable joints 309*a*, 309*b* by loosening clamping devices associated with the lockable joints 309*a*, 309*b*. In some examples, the controller 104 transmits control signals to unlock the lockable joints 309*a*, 309*b* by transmitting the control signals to brakes associated with the lockable joints 309*a*, 309*b*. The control signals release the brakes to unlock the lockable joints 309*a*, 309*b*.

The controller 104 drives the powered joint 116 while a position (and/or orientation) of the tool 114 relative to a reference (e.g., a reference comprising the reference point 118) is maintained. As depicted in FIG. 7A, to maintain the position (and/or orientation) of the tool 114, In some examples, the operator 700 manually inhibits motion of the tool 114 relative to the reference by grasping onto the tool 114, the actuation module 402, and/or the cannula 410 to maintain the position (and/or orientation) of the tool 114 relative to the reference. In some examples, the position (and/or orientation) of the tool 114 is maintained through a fixture that inhibits motion of the tool 114, the actuation module 402, and/or the cannula 410. The fixture receives and fixes the tool 114, the actuation module 402, and/or the cannula 410, thereby causing the position (and/or orientation) of the tool 114 to be maintained. The fixture is, for instance, attached to an object fixed in the environment 10, such as the support structure 306 described with respect to FIG. 3. In some examples, the controller 104 performs the operation 604 before the tool 114 is mounted to the actuation module 402. The actuation module 402, is for example, mounted to the coupling 414, and the operator 700 grasps the actuation module 402 while the controller 104 drives the powered joint 116.

The powered joint 116 is driven while the lockable joints 309*a*, 309*b* are unlocked and while the position (and/or orientation) of the tool 114 is maintained. In this regard, the tool 114 does not move (e.g. relative to a reference) when the powered joint 116 is driven.

In the example depicted in FIGS. 7A and 7B, the powered joint 116 corresponds to the joint between the linkage 405*a* and the coupling 414. Because the position (and/or orientation) of the distal portion of the linkage 405*a* relative to a reference (e.g., a reference comprising the reference point 118) is maintained, the proximal portion of the linkage 405*a* moves relative to the reference when the powered joint 116 is driven. In this regard, portions connected in kinematic series between the support structure 306 and the proximal portion of the linkage 405*a* move when the powered joint 116 is driven. These portions include, for example, the base 108 and the setup assembly 304. The base 108 is repositioned relative to the linkage 405*a* when the powered joint 116 is driven. If the tool 114 is centered during the operation 604, the base 108 is moved to a desired position (and/or orientation); in some implementations, the desired position (and/or orientation) is one in which the tool 114 is at a center of the range of motion for the yaw motion 422.

In some examples, the powered joint 116 corresponds to the joint between the linkage 405*b* and the coupling 414. Because the position (and/or orientation) of the distal portion of the linkage 405*b* relative to a reference (e.g., a reference comprising the reference point 118) is maintained, the proximal portion of the linkage 405*b* moves relative to the reference when the powered joint 116 is driven. In this regard, portions connected in kinematic series between the support structure 306 and the proximal portion of the linkage 405*b* move when the powered joint 116 is driven. These portions include, for example, the base 108, the linkage 405*a*, and the setup assembly 304. As the linkage 405*a* moves relative to the linkage 405*b*, the slot 419 in the linkage 405*a* is repositioned relative to the coupling 414. If the tool 114 is centered during the operation 604, the slot 419 is repositioned to a desired position (and/or orientation), for example, in which the tool 114 is at a center of the range of motion for the pitch motion 421.

In some examples, the powered joint 116 corresponds to the joint between the actuator 425 and the actuation module 402. Because the position (and/or orientation) of the actuation module 402 is maintained, portions connected in kinematic series between the support structure 306 and the actuator 425. These portions include, for example, the coupling 414, the linkage 405*b*, the base 108, and the setup assembly 304. The coupling 414 undergoes a roll motion when the powered joint 116 is driven, thereby causing motion of the linkage 405*b*, the linkage 405*a*, the base 108, and the setup assembly 304. The coupling 414 is repositioned relative to the actuation module 402 when the powered joint 116 is driven. If the tool 114 is centered during the operation 604, the coupling 414 is moved to a desired position (and/or orientation) in which the tool 114 is, for example, at a center of the range of motion for the roll motion 423.

In addition to the position (and/or orientation) of the tool 114, the position (and/or orientation) of the coupling 414, and the position (and/or orientation) of the actuation module 402 being maintained during the operation 604, in some implementations, a position of the remote center of motion 426 and a position (and/or orientation) of the cannula 410 (shown in FIG. 4A) relative to a reference (e.g., a reference comprising the reference point 118) are maintained. The linkages 405*a*, 405*b*, the base 108, and the setup assembly 304 are each movable relative to the reference during the operation 604.

While the powered joint 116 is described as a single powered joint, in some implementations multiple powered joints of the manipulator 102 are driven to reposition portions of the manipulator 102 and the setup assembly 304 relative to the reference and the relative to the tool 114. In this regard, the tool 114 can be centered within ranges of motion corresponding to two or more of the pitch motion 421, the yaw motion 422, and the roll motion 423.

At an operation 606, the controller 104 detects whether the desired motion envelope 122 of the tool 114 has been achieved (or, if the base 108 is in a desired location). Based on signals generated by the sensor system 506, the controller 104 determines when the desired motion envelope 122 is achieved. The controller 104 detects, for example, whether the base 108 is in a desired location to determine whether the desired motion envelope 122 has been achieved.

If the controller 104 does not detect that the motion envelope of the tool 114 is in the desired location, the controller 104 continues driving the powered joint 116 to reposition the base 108 in the operation 604. In some examples, the controller 104 continuously drives the powered joint 116 in the operation 604 while detecting whether the motion envelope of the tool 114 is in the desired location.

If the controller 104 detects that motion envelope of the tool 114 is the desired motion envelope 122 (e.g. of the desired shape and size, and in the desired location, or as close as achievable given particular constraints), the controller 104 indicates completion of repositioning at an operation 608. The controller 104, for example, issues a human-perceptible signal to the human operator to indicate the completion of the repositioning of the base 108. The signal may include, for example, one or more of: tactile, aural, or visual indications. Some specific examples include force feedback, beeps or tones of different spatial or temporal patterns, broadcasted language, lights of different colors or spatial or temporal patterns, and textual, symbolic, or graphical feedback.

After the desired motion envelope 122 for the tool 114 has been achieved, the lockable joints 309a, 309b are locked and the manipulator 102 is ready to be operated to perform an operation on the workpiece (e.g., in a surgical example, perform a surgical operation on the target anatomy). The controller 104 drives the powered joint 116 of the manipulator 102 to perform the operation. The controller 104 operates powered joints of the manipulator 102 and/or the actuation module 402, including the powered joint 116. The operation of the powered joints causes the pitch motion 421, the yaw motion 422, the roll motion 423, and combinations thereof, thereby moving the tool 114 to different locations within the desired motion envelope 122 to perform the operation. The controller 104 also operates the actuators of the actuation module 402 to effect the insertion motion 424 and the end effector actuation.

While the tool 114 is described to centered within a range of motion corresponding to one or more of the DOFs of the tool 114, in some cases, the tool 114 is moved to another position (and/or orientation) within the range of motion. For example, based on the input data received at the operation 602, the controller 104 determines the desired motion envelope 122 to be a motion envelope in which the tool 114 is biased away from the center of the range of motion of each of its DOFs.

Figure 8:
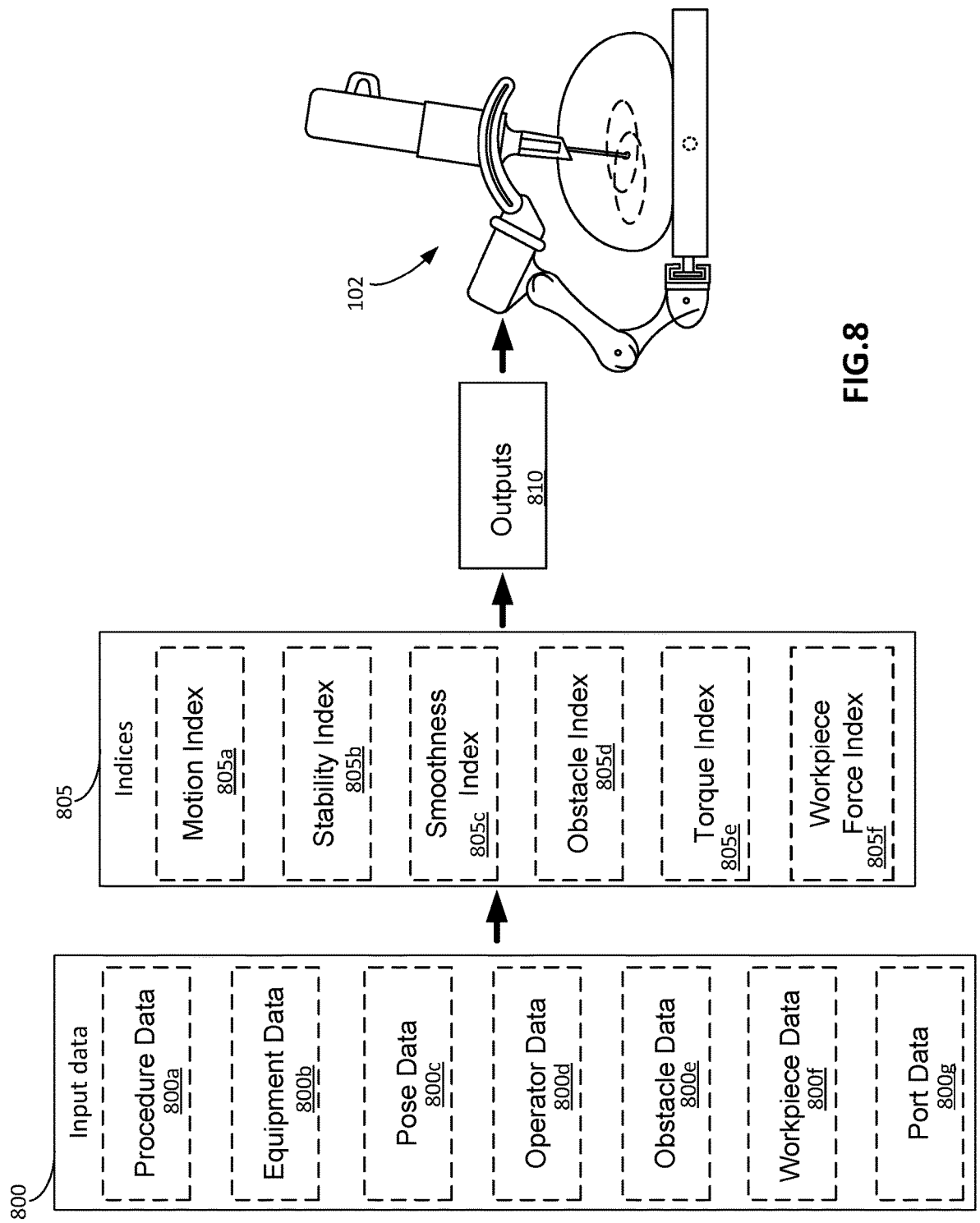
FIG. 8 is a diagram of example inputs for relocating a manipulator.

FIG. 8 depicts examples of inputs for relocating a manipulator such as the manipulator 102. For example, FIG. 8 depicts example input data that the controller 104 receives at the operation 602. Input data 800 include data loaded into memory associated with the controller 104, user-specified data, data generated by the sensor system 506, etc. The input data 800 include, for example, procedure data 800a, equipment data 800b, pose data 800c, operator data 800d, obstacle data 800e, workpiece data 800f, and port data 800g. The data 800a, 800b, 800c, 800e, 800f, 800g represent some examples of the data usable by the controller 104 to control the relocation system 100. Other types and contents of data may be appropriately used by the controller 104 to control the relocation system 100.

The procedure data 800a include data indicative of the specific procedure to be performed. For example, in a surgical example, the data 800a includes data indicative of the surgical procedure to be performed on the patient. The procedure data 800a can refer to specific requirements of a workspace, such as an area around the tool 114 should be able to access (e.g., in a surgical example, an area around the patient that the tool 114 should be able to access during the surgery, due to the specific surgical procedure to be performed on the patient). A procedure may require a predetermined extent of the workspace. In some cases, the procedure data 800a are generated when the operator selects the extent of the workspace before the repositioning operation. The operator can select the extent of the workspace in any number of ways. For example, the operator may input the data by highlighting or tracing in a graphical user interface. As another example, an operator can move the manipulator 102 (with or without a tool being held) to indicate the workspace desired, or by moving a substitute of the tool 114 to indicate the workspace desired. Example substitutes of the tool 114 include a device that represents an average tool that may be used during the procedure, a device that replicates a proximal portion of the tool 114 but not the entire shaft and end effector, a device that projects a visual indication of locations associated with distal ends of tools that may be used during the procedure, etc. Information about the desired range of motion of the joints of the manipulator 102 or the tool 114, or of the desired motion envelope 122, can be derived at least in part from such a demonstration. Pose sensors of a sensor system 506, for example, can provide data indicative of manipulator 102 configurations, tool 114 positions, or other system information form a manual demonstration by the operator of a desired workspace. The sensor system 506 can thus provide information about the desired range of motion of joints of the manipulator 102 or the tool 114, or of the desired motion envelope 122. The controller 104 or other computing system can then process this sensor information to determine the extent of the workspace demonstrated by the operator.

The equipment data 800b include data indicative of specifications of the equipment to be used during the procedure. The equipment data 800b can include data that specifies a range of motion for each of the joints of the manipulator system 300, e.g., powered joints, passive joints, or both. The range of motion can be a structural or mechanical limitation. In some examples, the initial motion envelope 120 of the tool 114 is estimated based on initial positions (and/or orientations) of the joints and the ranges of motion of the joints of the manipulator 102. The controller 104 determines desired positions (and/or orientations) for the joints within the ranges of motion that will enable the tool 114 to achieve the desired motion envelope 122. At the operation 604, the controller 104 drives the powered joint 116 so that the joints move toward the desired positions (and/or orientations) and the tool 114 is able to move through the desired motion envelope 122.

The equipment data 800b can also include information pertaining to the type of the tool 114 mounted to the manipulator 102. The type of the tool 114 may affect, for example, an extent of the workspace and an amount of torque necessary to perform an operation. The type of the tool 114 can be manually inputted by an operator. In some examples, the tool 114 may include a detectable tag that indicates the type of the tool 114.

The pose data 800c include data indicative of poses of the joints, links, the tool, and other components of the manipulator system 300. The pose data 800c includes the initial pose of each of the joints and/or links of the manipulator 102, the initial pose of each of the joints and/or links of the setup assembly 304, the initial pose of the tool 114, and the initial pose of the base 108. When the controller 104 executes the process 600 to position (and/or orient) the base 108, as the base 108 is moved, pose sensors of the sensor system 506 can generate signals responsive to motion of the base 108. During the procedure, based on the signals from pose sensors of the sensor system 506, the controller 104 can control the manipulator 102 to maintain the position (and/or orientation) of the tool 114 relative to a reference (e.g., a reference comprising the reference point 118) in accordance to remote center of motion methods described herein. In some implementations, the controller drives the powered joint 106 to move the base 108 in response to one or more signals from the sensor system 506 that indicates the position of the distal portion 112 (or device supported by the distal portion 112 such as a cannula or tool 114) is maintained. In some implementations, the controller drives the powered joint 106 to move the base 108 in response to one or more signals from the sensor system 506 indicating that the lockable joint 116 (or combination of lockable joints) is locked.

The operator data 800d includes data pertaining to the operator(s). In a medical example, the operator data 800d includes data pertaining to the medical team, e.g., the operators, carrying out the procedure. The operator data 800d includes, for example, information related to the capabilities, preferences for equipment layout, levels of experience, levels of skill, and other operator-specific attributes. In some examples, an operator profile is created for each of the operators before the procedure. A team profile alternatively or additionally is created for a particular team.

The obstacle data 800e include data indicative of poses (e.g. one or more parameters for positions or orientations) of the patient and obstacles in the environment 10 relative to the manipulator system 300. In some examples, the obstacle data 800e can include a map of the environment 10 inputted by the operator. The map can include locations of potential obstacles within the environment 10, such as other pieces of equipment (e.g., of the surgical system 200). The obstacle data 800e alternatively or additionally includes data from obstacle detection sensors of the sensor system 506. The obstacle detection sensor can generate signals indicative of positions, orientations, or poses of obstacles within the environment 10 before the procedure, or as the manipulator 102 moves about the environment 10 during the procedure. For example, referring briefly back to FIG. 2, in some example, the environment 10 includes multiple manipulator systems 300a, 300b or humans. The obstacle data 800e include locations of each of the manipulator systems 300a, 300b or humans, and the manipulator of each manipulator system 300a, 300b is repositioned based on a location of the other manipulator(s) or humans.

In some medical contexts, the workpiece data 800f comprises patient data and include data indicative of patient-specific characteristics. Such patient data can include data indicative of patient habitus and patient geometry. In some examples, the operator inputs the patient habitus and the patient geometry. In some cases, an imaging device can produce images that can be analyzed by the controller 104 (or by a computational system prior or during a procedure) to determine the patient habitus and the patient geometry. The imaging device may comprise part of a tool 114 or be separate from any tools 114. The imaging device may be inserted into the patient before the base 108 is repositioned during the process 600. The imaging device can produce images usable for estimating the patient habitus and the patient geometry. In some examples, the workpiece data 800f can also include data indicative of the pose of the patient relative to the manipulator 102 and/or the pose of the operating table 302 relative to the manipulator 102. The workpiece data 800f can include pre-operative images, such as x-ray images, x-ray computed tomography images, magnetic resonance imaging scans, and the like. In some cases, the workpiece data 800f includes intraoperative images or surface scans.

The port data 800g include data indicative of characteristics of the access port. The port data 800g can indicate a position and orientation of the access port, and the position and orientation of the access port can be indicative of a position and orientation of a reference (e.g., a reference frame, a reference location, one or more reference directions, a reference comprising the reference point 118, etc.). In some implementations, the port data is based on a pose of the manipulator 102 when a cannula coupled to the manipulator 102 is docked, when an operator indicates readiness for repositioning of the base 108, when a tool 114 is mounted, etc. In some medical implementations, a component such as the cannula 158 or the tool 114 is inserted through the access port on the patient, and the controller 104 can determine the position and orientation of the access port based on signals from sensors on the manipulator 102.

In some examples, the port data 800g can be inputted by the operator. If the tool 114 is not inserted into the access port before the controller 104 executes the process 600 to position (and/or orient) the base 108, the controller 104 can select the reference based on the inputted port data 800g. The reference is selected such that the tool 114 is positioned and oriented to be easily inserted into the access port after the positioning (and/or orienting) of the base 108 is complete. In particular, the tool 114 can be in a retracted position or configuration during the positioning (and/or orienting) of the base 108 and then translated axially to an insertion position such that the reference corresponds to the position (and/or orientation) of the access port.

In some implementations, one or more of the indices 805 can be selected, e.g., by the operator or in accordance to a default setting, to be optimized by the controller 104. The controller 104 optimizes the selected indices 805 by determining an optimal configuration for the relocation system 100. When the relocation system 100 is in the optimal configuration, the tool 114 has the desired motion envelope 122. In some cases, the controller determines the desired motion envelope 122 based on optimizing the indices and then determines the optimal configuration for the relocation system 100 to achieve the desired motion envelope 122. After determining the optimal configuration of the relocation system 100, the controller 104 generates output signals 810 to operate the manipulator 102 to achieve the optimal configuration and thereby achieve the desired motion envelope 122

As shown in FIG. 8, the indices 805 include, for example, a range of motion index 805a, a stability index 805b, a smoothness index 805c, a torque index 805d, an obstacle index 805e, and a workpiece force index 805f. Other indices may be appropriate. Each of the indices 805 represent an optimization goal for the controller 104. Based on the input data 800, the controller 104 computes values for one or more indices 805. The values for the indices are, for example, functions of the input data 800. The controller 104 can optimize the functions for the values of the indices based on the input data 800 received at the operation 602. The controller 104, for example, determines an optimal configuration for the relocation system 100 to optimize the functions. The controller 104, for example executes optimization strategies to determine the desired motion envelope 122 that optimizes the values for the selected indices. The optimization strategies include, for example, a gradient descent-based optimization strategy, a least squares-based optimization strategy, or other appropriate strategies. In some implementations, an optimization strategy for an operation is based on data from previous similar operations. The data from the previous operations include, for example, inputs collected during the previous operations, indices determined during the previous operations, and/or scores determined during the previous operations. In some cases, the optimization strategy is determined using a machine learning approach, such as, for example, artificial neural networks or expert systems.

The input data 800 and the indices 805 can be continually updated as the controller 104 performs the operation 604. In this regard, the controller 104 can continuously receive the input data at the operation 602 as the controller 104 drives the powered joint 116 at the operation 604. The values of the indices 805 can change as, for example, sensors of the sensor system 506 generate conditions of the environment 10 and of the relocation system 100. The desired motion envelope 122 can thus continuously change as the controller 104 drives the powered joint 116 and new input data is received by the controller 104.

In some examples, a single index is selected as a primary goal, and the desired motion envelope 122 is determined based on optimizing the value of single index. In some cases, a second index is selected as a secondary goal, and the desired motion envelope 122 is determined based on optimizing both the value of the first index and the value of the second index. In some examples, multiple indices are selected, and a weight is assigned to each of the selected indices. The weight is indicative of a priority of the index relative to other selected indices. A score is computed based on the weight for each selected index and the value for each selected index. The desired motion envelope 122 is determined based on optimizing the score.

A value of the range of motion index 805*a* is determined based on the range of motion available for each of the joints. The value of the range of motion index 805*a* may be computed based on, for example, the equipment data 800*b* and the pose data 800*c*. For example, the controller 104 can determine an amount of motion available in each of the two directions of a DOF for the current configuration of the manipulator 102, e.g., for the pitch motion 421, the yaw motion 422, or the roll motion 423. In some cases, the controller 104 determines the desired motion envelope 122 such that the tool 114 is movable a substantially equal amount in both directions of a DOF. In some examples, if the range of motion index 805*a* corresponds to the only index to be optimized, the desired motion envelope 122 is selected such that the tool 114 is centered with respect to each of its DOFs.

A value of the stability index 805*b* is determined based on the pose data 800*c* to determine the stability of the tool 114 in the current pose of the tool 114. The value of the stability index can be computed based on an amount of movement of the tool 114 while the base 108 is being repositioned. For example, during the positioning (and/or orienting) of the base 108, if the pose sensor of the sensor system 506 detects large movement distance, speed, or acceleration of the distal portion of the manipulator 102 (or of a cannula or tool 114 or other item mounted to the manipulator 102), the controller 104 can determine that the stability index is suboptimal. The value of the stability index 805*b* can thus vary during the course of the operation 604 as the sensor system 506 detects instability of the tool 114.

Alternatively or additionally, the controller 104 determines if the position and/or orientation of the distal portion of the manipulator 102 (or of a device held by the manipulator 102 such as a cannula or a tool 114) is not maintained relative to the reference. And, if the position and/or orientation is not maintained within a threshold or other maintenance criteria, the controller 104 can slow or stop further repositioning of the base 108. The controller 104 can also issue an alert to the operator to provide sufficient external maintenance of the position and/or orientation of the distal portion of the manipulator 102 (or of a device held by the manipulator 102).

In some implementations, the controller 104 slows, stops, or otherwise inhibits motion of the base 108 in response to a determination that a motion envelope of the tool is approaching a desired motion envelope 122 for the tool or if the base 108 is approaching a desired base location.

A value of the smoothness index 805*c* is indicative of the motion performance of the tool 114 and, in some cases, the motion performance of some or all of the joints of the manipulator 102. The controller 104 can estimate the motion performance by determining a resolution of motion of the tool 114 that is possible for the current pose of the manipulator 102 and the tool 114. For example, for a particular joint, actuation of the joint by an increment (e.g., a given applied voltage) may result in an amount of motion of the tool 114 that depends on the pose of each of the joints of the manipulator 102 and the pose of the tool 114. In some implementations, the value of the smoothness index 805*c* is computed based on the spatial resolution achievable as a function of pose and joint sensor position resolution. The smoothness index 805*c* can account for the size of the motion caused by the incremental voltage applied. In this regard, a smaller motion of the tool 114 from a given applied incremental voltage can result in improved motion performance of the tool 114 and greater smoothness of motion. The controller 104 can compute the value of the smoothness index 805*c* based on, for example, the equipment data 800*b* and the pose data 800*c*.

A value of the torque index 805*d* for the tool 114 is indicative of a torque that the manipulator 102 can exert on the tool 114. In some implementations, the procedure may require that the manipulator 102 be able to manipulate the tool 114 with a minimum torque necessary to perform the procedure. It may be beneficial in these cases to maximize the torque achievable by the tool 114. The achievable torque, however, can depend on the positions and orientations of the joints relative to the tool 114 as well as the position (and/or orientation) of the base 108 relative to the tool 114. The controller 104 can compute the value of the torque index based on, for example, the procedure data 800*a*, the equipment data 800*b*, and the pose data 800*c*.

In some implementations, instead of or in addition to a torque index, a force index indicative of a force that the manipulator 102 can exert on the tool 114 is computed. Furthermore, the torque index and/or the force index may account for forces and torques on joints of the manipulator system 300 such that forces and/or torques on a particular joint can be minimized during motion of the manipulator 102 within the workspace.

A value of the obstacle index 805*e* is determined based on the pose data 800*c* and the obstacle data 800*e*. The obstacle index represents a likelihood that the manipulator 102 may collide with nearby obstacles. In this regard, using the obstacle data 800*e*, the current pose of the manipulator 102, and the procedure data 800*a*, the controller 104 can compute the value of the obstacle index 805*e* to determine whether the manipulator 102 may collide with a nearby obstacle. The value of the obstacle index 805*e* may vary over the course of the operation 604 as new obstacles are detected by the sensor system 506.

A value of the workpiece force index 805*f* is indicative of an amount of force applied to, or applied by, the workpiece. For example, the value of the workpiece force index 805*f* may be computed based on the pose data 800*c*, the workpiece data 800*f*, and the port data 800*g*, and may be indicative of an amount of torque or force that may be exerted on a workpiece. The controller 104 can use the workpiece force index 805*f* to determine if the manipulator 102 or the base 108 are being moved in a manner that may apply force exceeding a desired amount on the workpiece. In a medical context, the workpiece force index 805*f* may indicate an amount of force applied to, or by, patient tissue. The controller 104 can use the workpiece force index 805*f* in determining if the force applied exceeds a threshold force for applying to the tissue of the patient.

Figure 9:
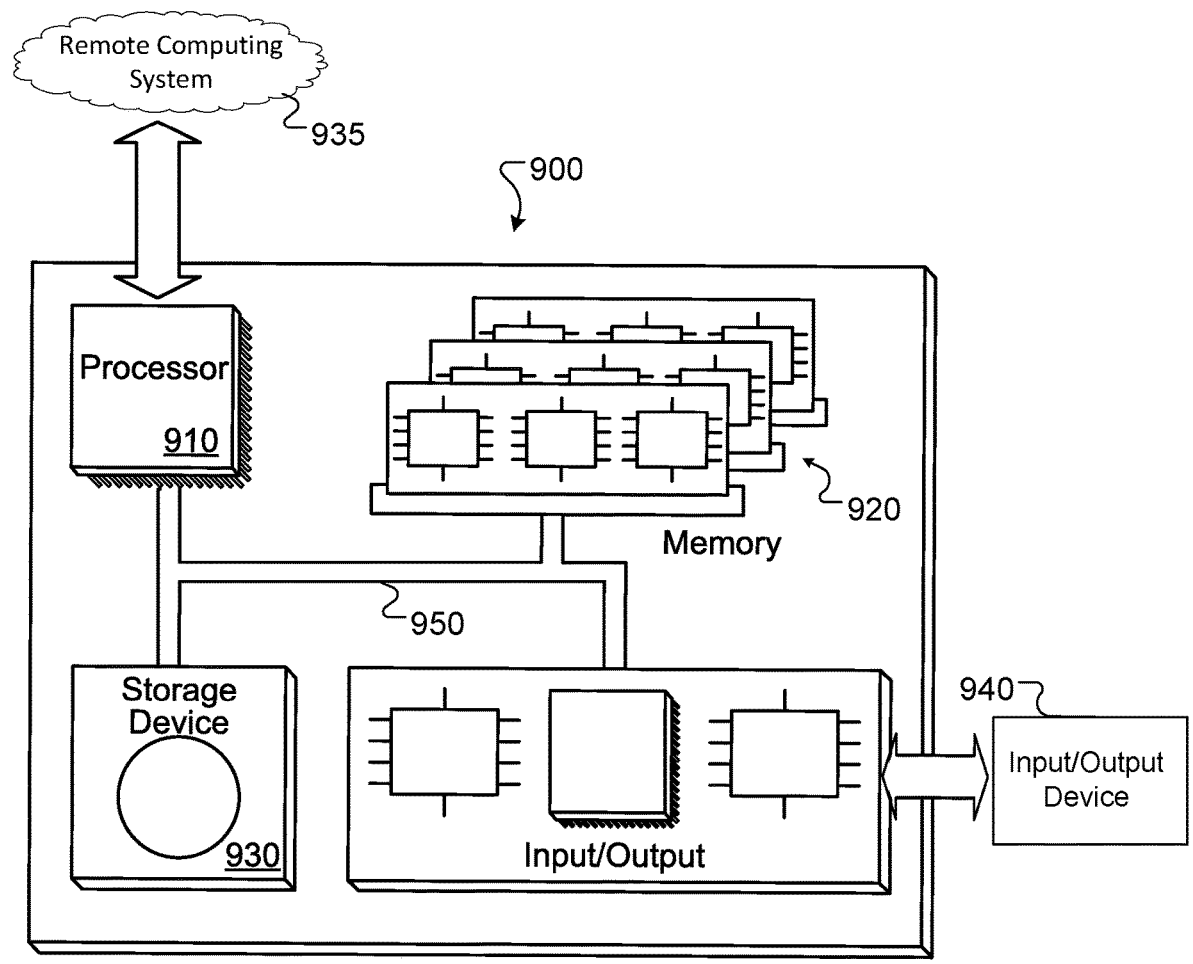
FIG. 9 is a diagram of a computer system that can be used to implement a controller described in association with any of the computer-implemented methods described herein.

Controllers and any associated components described herein can be part of a computing system that facilitates control of the insertion systems according to processes and methods described herein. FIG. 9 is a schematic diagram of an example of a computer system 900 that can be used to implement a controller, e.g., the controller 104, described in association with any of the computer-implemented methods described herein. The system 900 includes components such as a processor 910, a memory 920, a storage device 930, and an input/output device 940. Each of the components 910, 920, 930, and 940 are interconnected using a system bus 950. The processor 910 is capable of processing instructions for execution within the system 900. In some examples, the processor 910 is a single-threaded processor, while in some cases, the processor 910 is a multi-threaded processor. The processor 910 is capable of processing instructions stored in the memory 920 or on the storage device 930 to display graphical information for a user interface on the input/output device 940.

Memory storage for the system 900 can include the memory 920 as well as the storage device 930. The memory 920 stores information within the system 900. The information can be used by the processor 910 in performing processes and methods described herein. In some examples, the memory 920 is a computer-readable storage medium. The memory 920 can include volatile memory and/or non-volatile memory. The storage device 930 is capable of providing mass storage for the system 900. In general, the storage device 930 can include any non-transitory tangible media configured to store computer readable instructions. Optionally, the storage device 930 is a computer-readable medium. Alternatively, the storage device 930 may be a floppy disk device, a hard disk device, an optical disk device, or a tape device. This, the system 900 comprises a non-transitory machine-readable medium; the medium stores a plurality of machine-readable instructions which when executed by one or more processors (e.g. processor 910) are adapted to cause the one or more processors to perform a method or operations (e.g. any of the methods or operations described herein) for a computer-assisted system (e.g. the relocation system 100 or any other computer-assisted system described herein).

In some cases, the processor 910 is in communication with a remote computing system 935. The remote computing system 935 includes, for example, a remote server, a cloud computing device, or other computing device remote from the processor 910 and its systems. The remote computing system 935 includes computing resources remote from the environment of the processor 910, e.g., remote from the environment. In some cases, the remote computing system 935 includes one or more servers that establish wireless links with the processor 910. The remote computing system 935 includes, for example, a portion of a network-accessible computing platform implemented as a computing infrastructure of processors, storage, software, data access, and so forth accessible by the processor 910.

The system 900 includes the input/output device 940. The input/output device 940 provides input/output operations for the system 900. In some examples, the input/output device 940 includes a keyboard, a computer mouse, a pointing device, a voice-activated device, a microphone, a touchscreen, etc. In some cases, the input/output device 940 includes a display unit for displaying graphical user interfaces.

The features of the methods and systems described in this application can be implemented in digital electronic circuitry, or in computer hardware, firmware, or in combinations of them. The features can be implemented in a computer program product tangibly stored in an information carrier. The information carrier can be, for example, a machine-readable storage device, for execution by a programmable processor. Operations can be performed by a programmable processor executing a program of instructions to perform the functions described herein by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages. The computer program can be deployed in any form, including as a stand-alone program or as a module, component, subroutine, or other unit suitable for use in a computing environment. The computer program implements, for example, a fast genetic algorithm (FGA).

Generally, a computer will also include, or be operatively coupled to communicate with, one or more mass storage devices for storing data files. Such devices can include magnetic disks, such as internal hard disks and removable disks, magneto-optical disks, and optical disks. Storage devices suitable for storing the computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Alternatively, the computer can have no keyboard, mouse, or monitor attached and can be controlled remotely by another computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network. The relationship of client and server arises by virtue of computer programs running on the respective computers and having a client-server relationship to each other.

The processor 910 carries out instructions related to a computer program. The processor 910 can include hardware such as logic gates, adders, multipliers and counters. The processor 910 can further include a separate arithmetic logic unit (ALU) that performs arithmetic and logical operations.

A number of implementations have been described. Nevertheless, it will be understood that various modifications may be made. For example, the computer-assisted system may comprise one or more manipulators with redundant degrees of freedom. These manipulators, in some cases, are referred to as having excess, extra, or redundant degrees of freedom. A manipulator with redundant degrees of freedom has an architecture with more degrees of freedom than necessary to place the distal portion of the manipulator (e.g. manipulator 102) or a tool or other device mounted on the manipulator, if present (e.g. tool 114 or a cannula or other device in a given position. For example, in some implementations, the manipulator include a kinematic chain comprising a plurality of joints and links that provide sufficient degrees of freedom to allow a range of joint states for (1) a pose of the base (e.g. the base 108) and (2) a state of a distal portion (e.g. distal portion 112) of the manipulator (e.g. the manipulator 102) or of an end effector of a tool (e.g. tool 114) supported by the manipulator. In manipulators with redundant degrees of freedom, actuation of one joint may be directly replaced by a similar actuation of a different joint along the kinematic chain. Thus, one or more intermediate links or joints may be moved without changing a pose of the distal portion or a tool or other device mounted on the manipulator.

Accordingly, other implementations are within the scope of the claims.

What is claimed is:

1. A computer-assisted system comprising:
    a manipulator configured to support a tool, the manipulator extending distally from a base and comprising a distal portion;
    a lockable joint coupled to the base and located proximally relative to the base; and
    a controller operably coupled to a powered joint, the powered joint located distally relative to the base, wherein the controller is configured to perform operations comprising:
        driving the powered joint to move the distal portion while the lockable joint is locked, and
        driving the powered joint to move the base while the lockable joint is unlocked and a position of the distal portion is externally maintained.

2. The computer-assisted system of claim 1, wherein driving the powered joint to move the base while the lockable joint is unlocked and the position of the distal portion is externally maintained comprises:
    driving the powered joint while both the position and an orientation of the distal portion are externally maintained.

3. The computer-assisted system of claim 1, wherein driving the powered joint to move the base changes a motion envelope of the distal portion or the tool.

4. The computer-assisted system of claim 1, wherein:
    the position of the distal portion is externally maintained relative to a location of an access port through which the tool accesses a work site;
    driving the powered joint to move the distal portion while the lockable joint is locked comprises:
        moving the distal portion relative to the location of the access port; and
    driving the powered joint to move the base while the lockable joint is unlocked and the position of the distal portion is externally maintained comprises:
        moving the base relative to the location of the access port.

5. The computer-assisted system of claim 1, wherein driving the powered joint to move the distal portion while the lockable joint is locked comprises:
    driving the powered joint to move the distal portion while a position of the base is maintained by the lockable joint.

6. The computer-assisted system of claim 1, wherein the position of the distal portion is externally maintained by maintaining a position of the tool or a position of a cannula coupled to the manipulator.

7. The computer-assisted system of claim 1, wherein driving the powered joint to move the base while the lockable joint is unlocked and the position of the distal portion is externally maintained comprises:
    backdriving with the powered joint.

8. The computer-assisted system of claim 1, wherein driving the powered joint to move the base while the lockable joint is unlocked and the position of the distal portion is externally maintained comprises:
    slowing or stopping motion of the powered joint in response a determination that the position of the distal portion is not externally maintained.

9. The computer-assisted system of claim 1, wherein the manipulator is configured to couple to an actuation module and to support the tool through the actuation module, wherein the actuation module is operable to drive the tool, and wherein the actuation module comprises the powered joint.

10. The computer-assisted system of claim 1, wherein the manipulator comprises the powered joint.

11. The computer-assisted system of claim 1, wherein the operations further comprises:
    driving the powered joint to center the tool within a range of motion of the tool.

12. The computer-assisted system of claim 1, wherein driving the powered joint to move the base while the lockable joint is unlocked and the position of the distal portion is externally maintained comprises:
    determining a desired motion envelope based on a type of operation to be performed, a likelihood of collision of the manipulator, or a pose of the manipulator relative to a pose of a second manipulator of the computer-assisted system; and
    driving the powered joint to move the base toward a position that provides the desired motion envelope.

13. The computer-assisted system of claim 1, wherein driving the powered joint to move the base while the lockable joint is unlocked and the position of the distal portion is externally maintained comprises:
    driving the powered joint to adjust a position of the base based on a pointing direction of the tool.

14. The computer-assisted system of claim 1, further comprising:
    a setup assembly configured to couple the base to a table, the setup assembly comprising the lockable joint.

15. The computer-assisted system of claim 1, further comprising a sensor configured to generate a signal in response to detecting that the position of the distal portion is externally maintained, wherein driving the powered joint to move the base while the lockable joint is unlocked and the position of the distal portion is externally maintained comprises:

driving the powered joint to move the base in response to the signal.

16. The computer-assisted system of claim 1, wherein the operations further comprises:
   unlocking the lockable joint after driving the powered joint to move the base.

17. The computer-assisted system of claim 1, wherein the operations comprise:
   selectively unlocking or locking the lockable joint while driving the powered joint to move the base while the position of the distal portion is externally maintained.

18. The computer-assisted system of claim 1, wherein the operations further comprises:
   inhibiting motion of the base in response to a determination that a motion envelope of the tool is approaching a desired motion envelope for the tool.

19. A method for operating a computer-assisted system, the computer-assisted system comprising a manipulator and a lockable joint, the manipulator extending distally from a base, the lockable joint coupled to the base and located proximally relative to the base, the method comprising:
   driving a powered joint to move the base while the lockable joint is unlocked and a position of a distal portion of the manipulator is externally maintained, wherein the powered joint located distally relative to the base; and
   driving the powered joint to move the distal portion while the lockable joint is locked.

20. The method of claim 19, further comprising:
   determining a desired motion envelope for a tool supported by the manipulator, wherein
   driving the powered joint to move the base while the lockable joint is unlocked and the position of the distal portion of the manipulator is externally maintained comprises:
      moving the base such that a motion envelope of the tool is adjusted based on the desired motion envelope.

21. The method of claim 19, wherein driving the powered joint while the lockable joint is unlocked and the position of the distal portion is externally maintained comprises:
   backdriving with the powered joint.

22. The method of claim 19, wherein driving the powered joint to move the base while the lockable joint is unlocked and the position of the distal portion is externally maintained comprises:
   slowing or stopping motion of the powered joint in response a determination that the position of the distal portion is not externally maintained.

23. The method of claim 19, wherein the manipulator is configured to support a tool, the method further comprising:
   driving the powered joint to center the tool within a range of motion of the tool.

24. The method of claim 23, wherein driving the powered joint to center the tool within the range of motion of the tool comprises:
   driving the powered joint to adjust a position of the base based on a pointing direction of the tool.

25. A non-transitory machine-readable medium comprising a plurality of machine-readable instructions which when executed by one or more processors are adapted to cause the one or more processors to perform a method for operating a computer-assisted system, the computer-assisted system comprising a manipulator and a lockable joint, the manipulator extending distally from a base, the lockable joint coupled to the base and located proximally relative to the base, wherein the method comprises:
   determining a desired location for the base;
   driving a powered joint to backdrive the base toward the desired location while the lockable joint is unlocked and a position of a distal portion of the manipulator is externally maintained, wherein the powered joint is located distally relative to the base; and
   after the lockable joint is locked, driving the powered joint to move the distal portion.

26. The non-transitory machine-readable medium of claim 25, wherein driving the powered joint to move the base while the lockable joint is unlocked and the position of the distal portion is externally maintained comprises:
   driving the powered joint while both the position and an orientation of the distal portion is externally maintained.

27. The non-transitory machine-readable medium of claim 25, wherein driving the powered joint to move the base while the lockable joint is unlocked and the position of the distal portion is externally maintained comprises:
   backdriving with the powered joint; and
   slowing or stopping motion of the powered joint in response a determination that the position of the distal portion is not externally maintained.

* * * * *